(12) United States Patent
Nielsen

(10) Patent No.: US 11,072,796 B2
(45) Date of Patent: Jul. 27, 2021

(54) PLANTS COMPRISING A LOW COPY NUMBER OF RI GENES

(71) Applicant: KNUD JEPSEN A/S, Hinnerup (DK)

(72) Inventor: Kai Lønne Nielsen, Hinnerup (DK)

(73) Assignee: KNUD JEPSEN A/S, Hinnerup (DK)

( * ) Notice: Subject to any disclaimer, the term of this patent is extended or adjusted under 35 U.S.C. 154(b) by 7 days.

(21) Appl. No.: 15/749,418

(22) PCT Filed: Aug. 12, 2016

(86) PCT No.: PCT/EP2016/069235
§ 371 (c)(1),
(2) Date: Jan. 31, 2018

(87) PCT Pub. No.: WO2017/029214
PCT Pub. Date: Feb. 23, 2017

(65) Prior Publication Data
US 2018/0223294 A1 Aug. 9, 2018

(30) Foreign Application Priority Data

Aug. 14, 2015 (NL) .................................... 2015306
Aug. 17, 2015 (NL) .................................... 2015312

(51) Int. Cl.
*C12N 15/82* (2006.01)
*A01H 6/32* (2018.01)
*A01H 6/14* (2018.01)
*A01H 6/72* (2018.01)
*A01H 1/04* (2006.01)
*A01H 4/00* (2006.01)

(52) U.S. Cl.
CPC ........... *C12N 15/8205* (2013.01); *A01H 1/04* (2013.01); *A01H 4/005* (2013.01); *A01H 6/1448* (2018.05); *A01H 6/324* (2018.05); *A01H 6/72* (2018.05); *C12N 15/8261* (2013.01); *Y02A 40/146* (2018.01)

(58) Field of Classification Search
None
See application file for complete search history.

(56) References Cited

U.S. PATENT DOCUMENTS 9,253,952 B2 * 2/2016 Christensen ............. A01H 3/00
10,329,573 B2 * 6/2019 Christensen ............. A01H 3/00

OTHER PUBLICATIONS

Christensen et al (2008, "Transformation of Kalanchoe blossfeldiana with rol-genes is Useful in Molecular Breeding Towards Compact Growth", Plant Cell Report 27(9): 1485-1495).*
Britton et al. (2008, "The Oncogenes of Agrobacterium tumefaciens and Agrobacterium rhizogenes", In T. Tzfira and V. Citovsky (Eds.), Agrobacterium: From Biology to Biotechnology (pp. 523-563). New York, NY: Springer Science Business Media, LLC).*
Christensen et al (2008, "Transformation of Kalanchoe blossfeldiana with rol-Genes Is Useful in Molecular Breeding Towards Compact Growth", Plant Cell Report 27:1485-1495).*

* cited by examiner

*Primary Examiner* — Vinod Kumar
(74) *Attorney, Agent, or Firm* — Browdy and Neimark, PLLC

(57) ABSTRACT

Described is a plant transformed with one or more genes originating from the Ri plasmid of *Agrobacterium rhizogenes* by infection with *A. rhizogenes* comprising the Ri plasmid, or being progeny of such a plant, said plant or progeny comprising, in the genome thereof, 1 to 5 copies said one or more genes originating from the Ri plasmid. Further, the use of such a plant or progeny thereof as ornamental plants, the use as field crop species, for food extracts, cosmetics, perfumes or as medicinal plants is disclosed. Further disclosed are methods for the preparation of such plants. Said plants display an intermediate height and/or with a higher content of metabolites without significant reduction of flower number or flowering time delay as compared to control plants void of *Agrobacterium rhizogenes* sequences.

9 Claims, 15 Drawing Sheets

Specification includes a Sequence Listing.

ABSTRACT

SEQUENCE LISTING

```
<160> NUMBER OF SEQ ID NOS: 12

<210> SEQ ID NO 1
<211> LENGTH: 19471
<212> TYPE: DNA
<213> ORGANISM: Agrobacterium rhizogenes

<400> SEQUENCE: 1
tggcaggata tattgtgatg taaacagatt agatatggac atgcgaagtc gttttaacgc      60
atgctttatc gaatataaaa tgtagatggg ctaatgtggt tttacgtcat gtgaataaaa     120
gttcagcatt cgtttaataa tatttcaata tcggtgtcta gagaccgtg gatttgtata      180 gtcagcacca tgtatgaat ctataaaata ttgtatctcc aattgcaatt caatcgatat      240
aagaaattaa tacaagccgt tcatatagta aggttgccaa tggcattcaa taacgaccgt     300
acagttgccg ctatattaat ctacgtgcca tttcttaaat aaagataggc gaatgactat     360
cgaaaataaa acaattatta atgagtgaaa acgtattgca caaataaaga ttcattatgg    420
ttggctcaaa ttttggctct ggtgctcgat gacgtcgaga tgaggacagt agtgatcaac     480
ttggcggtcg ataccttggt tacgccactc ccagagtgcc atgtcgtcct ccgagcggtc     540
tgagataacc cagtcggcaa ttgctgctgc attgccgggc gttccccaac cacgacgaat     600
atgctttcgt tcatctaact cgcgtcgcac tgccctccca gtcatgaagt caaagccaaa     660
ttctaccctc tctccatttc ccagctcagt cgagaaatcg taacacctcg tggcagctga     720
cagtttcaga aagggggcgta tccctcgaac tccagggtcc tctttcacat agttagcaag     780
gcgtactgct gcataatctg cgttgaaggc tctgatgact acaggatcct cggacaagcc     840
caattgatca gggcgaaccc tcgcgctcat aatatgaatt gcgacgaccc ttgcttcctg     900
```

```
tcggagcatc gaatcaatcc aagccttccc tgcggcatag aggtcatcga ctgcgatgtc    960
atcaagatcg agtagctttg ccaacctagg aagttcttga ggaaaaatca ccggcatgac   1020
agcaaccgtc tctcgccagt cagttgccgg actggcttcc ctaacgccat ccacgaatgc   1080
ctcaccgctt gcgtatttga atgtgtaaaa gagaaggacc actctttggc ggtacttcgg   1140
acgccggctt agccacgcgg caataatgtg ggcctcaaac tcacgaccat ccaaaaatat   1200
agtcgcgcct ggattgacct cgctggcctt gtcgagaaga ggttccaaaa agggaacggt   1260
gtctttcgta atagtactta aatctgtgag ttcgccatgc gaaacctctc gaacgattat   1320
cggcgtatcc ctgacatcag ctgaatgaaa ttctcggacg agtttgtcgg gcaaagtgga   1380
gacccgccac gtgttgaagt cgtgggaaac gatgggcaca tcgtcgccgg tgagtgcggc   1440
atcgagctca gagaggttcc gcctgccaac ctcaccgaga gcagctaaca acgaagtttc   1500
ggtgcattcc tgtatccctt tacccagatt atacatgccc cggtgttcga taacttgaag   1560
aggcagtggc tcctcaagat gttcaaggag gtggggtaca gagtgccggg cgaggacctc   1620
atccaccgtg acaccaaccg ggagatccca ttcgagtttc cactggggcc agcatgtgcc   1680
cgcgacggca aaaggtttgc gctggcaaag aacccggctg ctgcaggtgg acctatcctt   1740
acccatggca atggggtttt gctaaaaagt caggcacttt actgggcaat tgatagggtg   1800
ggattgcgtt attaactgtt ctccagcggg aatctttatc tttattgaaa tgctaaagca   1860
cttagataaa atacagctgt accgcaatat aaaatagtag gataatgtaa tatgtgtatc   1920
gagaatacga caagctaata taatctagcg tcaaattgca ataatttaaa tcaaaactac   1980
tgatgaaata ataaaagatg gtcaatttt attggtagga gttgtcgaaa gattcgacgg   2040
acggccatta caatacatag gtgcaagaag taaaacagga agggaaacgg aaaacagtgc   2100
tataaaaaag cgacagatcg cggcgatcac tgactgcgat cgggaagaag ctcgccaagt   2160
tcaccgagaa tagcagagag cgcatcctca tcgggtacta cgaacacatt cgtcccagag   2220
ggctttgttt cagctgcgcc aacccagaaa gcaaggccat tttccaagtt gccgatggcg   2280
gtcagcatgt tttgattgtt gctgccgttt ccacaagcga tgtgaaggcc gatcccgtga   2340
gagaggccct tgacgaaggt gaaatagcct ttggattttc caactgtttc aacgggcact   2400
agatattgac cctctggcgc ggcaaccacc ttgaatttgc gagatgactg gttgccgatg   2460
agcgaagaaa gcatttctcc ggcttctttg taagatttgt gagattccca catttgacag   2520
ccgtagaaat gccccatcgg aatgttgcgg attcccggga tgccaccaaa tttgttctcc   2580
atagccgcgt gaacggcttg ccagttgggc agggagaaag aatcgaagcg atcatctttg   2640
tagatcgtga ccattccatc atttccctgg aatccgatat tttcaatggc gctgaaaact   2700
gaccttgcga tttcttcgca ttcccgtgcg gatgtgagca attgataatg gcccttgcag   2760
gcgatcctgg tcaaattggc gatgatgttg atggcaggat taatatccca acactggtga   2820
tttcgatctt gcttaaaggt ggtaccatcg ccgtcgaagg cgagcagggc ccggagagat   2880
gaatcggcaa gactgcgtcg gacccgctcc gcggcgtcgg gaatgaggct gataagagac   2940
atatccaaag gtgtttgtgg gtaacgggct gctcaatgaa gccttaaatg caacgcaaca   3000
tatgtaagga tgagttgact tattggagag agaaatagga atgagctggc cagccattat   3060
caacgtgggg ccatgctgac aatgtttacg tgaaaggctc aactacctcg aagcagacct   3120
ctatattcgt tgactttatt actgaacaag aagttgcttg ccactcattt tcttaaatct   3180
tgcccttcct gcgcctcgct atcatgcccg ccaacgacgc gacatgcgct gccgcgattg   3240
```

```
ccttccccga gggcaactgg aaggaagaac ttgatgcgct ccgcaccttg tgtgaccccg   3300
tcgaggtggt taaggtcgca gtcggcagag gtcttagcgg catatgtaat gttgttgcag   3360
caatgaatcc cacaaaggtg aggggcctcg gcgatgtcat cgggcagatg ccggctctta   3420
atcaccgtat tgctgccgcc gccggcgaaa ctccggtgcg agaccttgga ataggttacc   3480
agtgcgcaat ctgccacccc gacatagcca gtgcgatgtt agccacttct gaggggatca   3540
gccacgttct ccgtgaaagg attgagaaag aagttgaccg ggacattgga gaaggcgcca   3600
ccgtctgcat tttcgttcag ccgagaatga gctccaaggg ctctccagtt tctgtccatt   3660
tcaccctcca gtttgcgaga tctgaactc ttgtcgatgc cagaatgatg gagagttaca   3720
atttcatgaa aggcaatggc acagtgaccg caccggattt gaaaagtcat tggaagaagc   3780
acggtattga caggccaggc ccacgtccgc ccacgtccaa gtttgaactc ctcttcgccg   3840
ctgtccccga caacagtaaa cttgccgcca ccgattttac ccatctcggc cctgtcgagc   3900
gtgataagga actactcggc agcacggtat tcgggattgc cgctaagaaa cctggtacga   3960
tcgtttatcc gtgcgaaaag gttctctgtt tggaggtcga cgtacacgcg catcgcgccc   4020
tagaagtact tcaccgcctt ggggaacagg cttatagcaa tggccgtggc actagcttcg   4080
gtcttcacac cggtccgtcc tcttgcctta atctttccgc cgccgcgctc gctacatttt   4140
tcaaacgctc ggatctctgt tcccttccat tgagtgatgc ttttgtcctt ttctgcgacc   4200
cgccaccgcc tacagcgcca agaaagatgg ccttccgatc actgccttct cccccacgag   4260
caccaatcag ttcgaactcg tagagcctca ggtcgtcaag gcatatgttc tcggacttt     4320 cgacgcgccg acgatggtta cgccccgcga caaaacgcga gccagcttct gcagccaata   4380
tgtacgtttc cgtgaaccgc atccctgtga agagttcaat gaaattggag ttttgatcct   4440
cgatgctgct gctaaaatgc tcgaacgtta tgcaaaattt ctagaagatg gtggaagaga   4500
tgatgatgaa atggcgaaca taatagatgt atttgggttt tgtcttaact agtggattga   4560
ttgaaacaaa ggagtccgag ttgggattcc ctttcggtct tcgtcgtgca acgatatcgt   4620
atgcgtacag gtatcacatt taacgttgct gcggcggacc gagcccgctt ggaagcgatt   4680
gttgcagctc caacttctgc tcagaagcac gtgtggcgag cgaagatcat cttgatgagc   4740
agtgatggct cgggaacggt cgcgatcatg gaggcaaccg gtaaatccaa aacctgtgtc   4800
tggcgctggc aggagcgctt catgactgag ggcgtcgatg gccttttgca cgacaagagc   4860
agaccgcccg gcattgcgcc gcttgatggc gaactcgttg agcgtgtcgt cgcactgacg   4920
cttgagacgc tcaacagga agcaacgcac tggactgttc gtgcgatggc caaggccgtt   4980
gggattgcag cctcttcggt tgtgaagatc tggcacgagc atggtcttgc gccgcatcgc   5040
tggcgctctt tcaaactgtc gaacgacaag gcctttgccg agaagcttca cgacgtcgtt   5100
ggcctctacg tctcgccacc ggcccatgcc attgtcctgt ccgtcgatga aagagccag    5160 atccaggcac tcgatcggac gcaacccggga ctccccttga agaaagggcg cgccggcaca   5220
atgacccacg attacaagcg ccacggcacc accaccctat tgccgccct caacatcctc    5280 gacggctcgg tgatcggccg aaacatgcag cgtcaccggc atcaggagtt catccgtttt   5340
ctcaacgcca tcgaggcgga actgccaaag acaaggccg tccacgtcat tctcgacaat    5400
tacgcgaccc ataagcagcc gaaggtccgc gcctggctgg caaggcatcc gcgctggacc   5460
ttccacttcg tcccaacatc atgttcatgg ctgaacgccg tcgagggatt cttcgctaaa   5520
ttgacacgtc gacgtctgaa gcacggtgtc tttcattccg tcgttgacct ccaggccacc   5580
atcaaccgct tcgtcagaga gcataatcag gaaccaaagc cgttcatctg gagagcagat   5640
```

```
ccagacgaga tcattgcagc cgtcaaacgt gggcaccaag cgttggaatc aatccactag    5700
cgtatgaaca gtaataagaa aatcccgatt gtgaatagtc ccaatttcaa atgtgtccgt    5760
gtgtaatttg cgtgtcttca gttgaatttc ctttaataat atcaaatatt caattgtgaa    5820
aagttgtatt ggttcaggtt caagctttcc gaatttgttg aattttattc cctgttttca    5880
atttgttgac ttgtttggga gacaccttt ttgtgtttcg tgaacatgtc accccttcgg     5940
tatacattag cctacaaagt aaataacgtt gataaatgtc actcatgttg taataaaatt    6000
gagcttatta tgtataacca gaccctgtgt taatctaatt acaaagaaat tcatcattct    6060
cccaagcaat cctgagtagc tgcgtgatgg atcttccata tcagcgccca cgtttcaccc    6120
cgtttgccgt cacccatcca cgtagtggag tcaacctgaa ccgtgcaatt tctcaggcct    6180
ttgtctgcta tgatcagttc tgcgaacggc tcttgcgata tcagcaaagc tggacggatt    6240
gggtgttcga ccacggattt gcagaagcca ttgaagacgt ggcgctggtg ttccaggttg    6300
caccttgcct tcatggcccc cgaataggcg cgctcgaagt gttgatacct cgtcgcaccc    6360
aggtcttcat ttatatgtcg aacaaccaat tgcagcgctt tgttgcacac cagtgcattg    6420
ctcaacttgg cgacgccgtg cttgcttgca tgatcccgcc ctacgcgagt gacctctcgc    6480
tgcaggaaat ggctcgggcg cacaacagat tttgcccagg cagttacacg aggtccgcag    6540
acgtacagtg ctttatcgcc atccaactca gcagccgatt cgttgaggag ggcacatgta    6600
acgtgcacgg gcgaaatggc ttaaaaagaa cctgccgctt ctttcgtcgc cctgctgagt    6660
tcttcagccg ttatgacatc gttgccattg ggccggtgct cttccatgat gaactggatt    6720
gcccagcaaa ctgcaatgag cctctttcct gctttgacct gcggtacgac tatcaggttt    6780
tcctccagga gtgcgatgcc catgatggtg tggggcatta tccggaaggc gcaccactac    6840
ctagtgttgc catcgtagga ggcgggctgt ctggccttgt tgctgccaca gaactacttg    6900
gcgctggcgt caaggaaatc actcttttcg ataccgttga tgagatccgt agttttgggg    6960
catcgccgat gccaaacggc gacgctcacc aggccttgac gtcgttcggt gtcatgcctt    7020
tctccgccaa ccaactttgc ctgtcatact atctggataa gtttagaatt ccgtccagcc    7080
ttcgttttcc ttgtgccggc aacgaccaca cagcactata tttccgccag aaacgctacg    7140
catggcacgc ggggcaagct ccgccgggga tatttcagcg gtacatgtc ggatggaaga     7200 cactactcta ccaagggtgt gaacggaatg gcaggagact gatggctccg atggatatct    7260
ctttcatgtt gaaagagcgt cgtcgtgatg aagcctcaga agcacggcag ctttggctcc    7320
gagagttcgg aaaattcact ttccatgccg ttttggtcga gatcttcagc tgtggtaatt    7380
cgagtcctgg tggcaaggca tggcaaacac cccatgattt cgaggctttc gggatactga    7440
ggttgggata cggccgagtt tcgtcctatt acaacgtgtt gttttcaacg atcctggact    7500
ggattatcaa tggctacgag gaggaccagc atctttctat tggtggggtt caacttttgc    7560
aggctctgat gcgcattgaa atattccaga aaagccatgc gaaagcacga ctctgttttg    7620
atcccgtgcg tggaatagcc aaggagggcg ggagattgaa ggtatgcttg aaacacggtc    7680
attcgcgtgt ttttgaccag gtcatcattg gcggcagtgc tgaggccgct acagttgata    7740
acagactggc cggggatgag acttccttca gctacaatat cgaacccgcc gtcggaaact    7800
cgtctgccgc tgtcaattca gcactcttca tggtcacgaa gcaaaagttt tgggttaact    7860
ccggcatccc agcagtgata tggaccgatg ggcttgtccg tgagctgtgt tgcattgaca    7920
tcgaatcgcc agctggagag ggccttgtcg ttttcacta tgctttggat gactatctat     7980
```

```
cccggccgat cgagcatcat gacaagaagg gacggtgctt ggaattggtc agggagcttg    8040
ctgctgcctt tcctgaactg gcttgtcacc tggtcccagt caacgaagac tacgaacgat    8100
atgtcttcga cgaccaccta acggatggtt ttaagggagc tttgtggagg gaaaattctc    8160
tggaaaaagg tcagtatatc caggatctgc ctgggaataa ttttcctatt ggggatcacg    8220
ggggagccta tctgattgac cgtgacgact gcgtcaccgg agcctcgttc gaggagcagg    8280
tgaaggcggg catcaaagcg gcctgcgccg tcatccgcag caccggcggg acgtctctt    8340 cactccaacc ggtggactgg aataaaaaat agaaatttcc tgattaagtt atagtcaatg    8400
tactattgcg tgttaatccc gtaggtatgc aagctgcacc ggcagcatca taatttgatg    8460
ttccatcaat aaattaaggt gcccgttcat tgtgtattac attatgtatg tttatcaaaa    8520
atataatcga agtccatttt aagtctgata ttaattggaa ttccaaacga ttccttgatg    8580
cctatcttcg ctatgattgt atggtaataa agtctccaca tctcccgaaa aatgctttcg    8640
tgatttactt gtctctcacg tgctttcgca tcttgacagc caaaagtggg caacttgaga    8700
agagtattaa ctggccacgc aactcgagat attcccacta accccaatga cgtcattgca    8760
ctcgtcacgg gtagcagccc cacttgcctt tgccacttta ttaattcttt ggcccactgg    8820
ccattaattg gcacctacat atattagtgg agaagataaa gtgtcactat cgtttcctgt    8880
tcaattttga attttgcaag gatttcatgt tgtcaactac acagcttgaa aggaaatccg    8940
caatcaacgg agaaacgtca acatctcgac aaaaaaagaa tgcttcatca ttgcgtagac    9000
tgcatattga ccgctccttt cggcgctggg cctgctttta ctgttgccta gcgttcggac    9060
agccaccaga gaatgggcta tatagatcct ttcatcaaac caaaacatta ctaagatcat    9120
gctgtaacgc ttcaatacgg tgagtgtggt tgtaggttca attattacta tttttgaagc    9180
tgtgtatttc ccttttttcta atatgcacct atttcatgtt tcagaatgga attagccgga    9240
ctaaacgtcg ccggcatggc ccagaccttc ggagtattat cgctcgtctg ttctaagctt    9300
gttaggcgtg caaaggccaa gaggaaggcc aaacgggtat ccccgggcga acgcgaccat    9360
cttgctgagc cagccaatct gagcaccact cctttggcca tgacttccca agcccgaccg    9420
ggacgttcaa cgacccgcga gttgctgcga agggaccctt tgtcgccgga cgtgaaaatt    9480
cagacctacg ggattaatac gcatttcgaa acaaacctac gggattaata cgcacgtggc    9540
tggcggtctt cgattcattt ccacgccgga gatgatatcg aatatgttct gttaagttaa    9600
aataagctgc gagccatggc gcgattgtcc tgttttatta atatagtact ttaacgtctc    9660
tttagagcgt ttgtgtaatg tcgtgaaaat gttttatgtc aaatgtactg ttgaactata    9720
atattataag tccaggtgtg tcgttgttgt tgatactgca atatatgtgt agtagattag    9780
atagtcatat gagcatgtgc tgttttttggc aaaattcagc agcaggatca acacagaaga    9840
aaatatttag tacaagaaaa taggtcaaca cattacaacg tacgctacaa ctcccaaggt    9900
tctgtgtcac agactgcggg agggtacata gaacttatga caaactcata gataaaggtt    9960
gcctgcaggg ggagttcaag tcggctttag gcttctttct tcaggtttac tgcagcaggc   10020
ttcatgacgc cctcctcgcc ttcctgatca ggccccgaga gtcgcagggt taggtctggc   10080
tccggtgagg aggcggccgg acgtgatatc ccgagggcat ttttggtgaa ttgtgtggtg   10140
ccgcaagcta caacatcata ggggcggttt tcagtccctc gccgcagaaa gaaggtgcaa   10200
gctacctctc tcccgtaaac gttggtcact tttaactcca gcaagtgaat gaacaaggaa   10260
cttgcgaaaa tggcgatgaa gcattctaaa tcaggttcct ccgtgcggct gtgcggccaa   10320
gcaaggttgt gaacacggag catctcctgg agggcgagct cgctccgata tggttgaatc   10380
```

```
gttgtcgcca gcacggcctc cattccaaat gtaatggatt gttccttcag cactttctgc    10440
atcttctcgc gagaaagata gacaaataca tgttggtcgt tttctcgagc cagatccggc    10500
tgactaacaa acataggagg atgatagcag actttgttct tcaagagctc agctagttgt    10560
ttaagtatat atatcggtgg agagttttcc ttcaaatcta gcactgcaag agcccatcgt    10620
ttctggaaat gcaggagggg tttgctatag tcacggctat agattgcaaa agcaaatcgg    10680
atcccctcga ataggtttat ctggctccat gctggagtga gatctactgg ttgaaatcgt    10740
ggaaggaata gcaatttggg atccattgtg atgtgagttg atagttacg aaaaaggcaa     10800 gtgccagggc catttaaaat acggcgtcgg aaactggcgc caatcagaca cagtctctgg    10860
tcgggaaagc cagaggtagt ttggcaacaa tcacatcaag atcgatgcgc aagacacggg    10920
aggccttaaa atctggatca agcgaaaata ctgcatgcgt gatcgttcat gggttcatag    10980
tactgggttt gcttttcttt gtcgtgttgt ttggccttag cgaaaggatg tcaaaaagg     11040 atgcccataa ttgggaggag tggggtaaag cttaaagttg gcccgctatt ggatttcgcg    11100
aaagcggcat tggcaaacgt gaagattgct gcattcaaga tactttttct attttctggt    11160
taagatgtaa agtattgcca caatcatatt aattactaac attgtatatg taatatagtg    11220
cggaaattat ctatgccaaa atgatgtatt aataatagca ataataatat gtgttaatct    11280
ttttcaatcg ggaatacgtt taagcgatta tcgtgttgaa taaattattc caaaaggaaa    11340
tacatggttt tggagaacct gctatagata tatgccaaat ttacactagt ttagtgggtg    11400
caaaactatt atctctgttt ctgagtttaa taaaaaataa ataagcaggg cgaatagcag    11460
ttagcctaag aaggaatggt ggccatgtac gtgcttttaa gagacccat aataaattgc      11520 cagctgtgtt gctttggtgc cgacaggcct aacgtggggt ttagcttgac aaagtagcgc    11580 cttttccgcag cataaataaa ggtaggcggg tgcgtcccat tattaaagga aaaagcaaaa   11640
gctgagattc catagaccac aaaccaccat tattggagga cagaacctat tccctcacgt    11700
gggtcgctag ctttaaacct aataagtaaa aacaattaaa agcaggcagg tgtcccttct    11760
atattcgcac aacgaggcga cgtggagcat cgacagccgc atccattaat taataaattt    11820
gtggacctat acctaactca aatatttta ttatttgctc caatacgcta agagctctgg      11880
attataaata gtttggatgc ttcgagttat gggtacaagc aacctgtttc ctactttgtt    11940
aacatggctg aagacgacct gtgttctctc tttttcaagc tcaaagtgga ggatgtgaca    12000
agcagcgatg agctagctag acacatgaag aacgcctcaa atgagcgtaa acccttgatc    12060
gagccgggtg agaatcaatc gatggatatt gacgaagaag gagggtcggt gggccacggg    12120
ctgctgtacc tctacgtcga ctgcccgacg atgatgctct gcttctatgg agggtccttg    12180
ccttacaatt ggatgcaagg cgcactcctc accaaccttc ccccgtacca gcatgatgtg    12240
actctcgatg aggtcaatag agggctcagg caagcatcag gttttttcgg ttacgcggat    12300
cctatgcgga gcgcctactt cgctgcattt tcttttccctg ggcgtgtcat caagctgaat    12360
gagcagatgg agctaacttc gacaaaggga aagtgtctga cattcgacct ctatgccagc    12420
acccagctta ggttcgaacc tggtgagttg gtgaggcatg gcgagtgcaa gtttgcaatc    12480
ggctaatggt tagtcgatgg gctgacgagt ttgatgtcag gagaagctga gtgtgtcact    12540 tgtttcccctt taagaagtat taatgtaata aaaatcaaga tctggtttaa taactggata    12600
cttgatttca tcgcgctttt tttgaataaa tgtttgttgt cttgacttta agatatcctt    12660
tgaaatttgc gttattcgta tttcgctttt ggttatttcc aaaagacttt gctcagtaag    12720
```

```
atcaaacgtt tgtatttctc cgggccacaa tatttgacct atatgcactg gcccacgcgc   12780
cgcaatagat gaaaattgcc aaaattagct atcggtcttc tgaaaagaag ggccgacatg   12840
ttttcataga ccatgcaaag tcatactacc tgaaactgat aaataacgac aaagaaagta   12900
gcctatttaa aagtcgctat agcatgaatt caacacaagg aaaccaaaag tcggaaggaa   12960
gactttaatc ccggattatt tggacatgat aggagctatg gggcaacgtg tcattttcat   13020
gagtgttgaa tgattttctg tagcaaatag aaaacgtttt ttaaaacgat gtggccttgg   13080
agtaatcagc ggaagaaatg gtcatgctca gataatttcc gttgctgacc tcgcaaccaa   13140
cccctttaaa tacctctgct gcccatgcat tttgccaagt taacctaaag tggcagctga   13200
atggctcgtt attgcagtgg tggctctcaa cggcttcatg tcgatgattt tcgttggatc   13260
aaggagccca ctcgactgaa ggctcagctt attaatgtgg tggagaccta caaggctgca   13320
caaacagaga cgttaaagta ctatatatca tctgcaactg agcgtgtggc tcatgtggag   13380
gcagccgagg tcaacaatgc ggaaatggag ctgcatcctg ctgggttgaa gtaccctctg   13440
tccttcgtct ttacctccct ggccgtggct acagcctgca aggagaacaa gcatctcttg   13500
tgcgaggagc atttggaggg ggacttgata tcgtgcgtcg ttcctcccta tcagacaaat   13560
gtctcactcg ctgctttaag ggagctccac aattccattt cggaggaggg gtaccaggaa   13620
caagcagaca tggattattt tgtggcgatc atcccaaatg ataatttcga ctatcagagc   13680
tgcgaaatcg acacacgaag ttgcggtaaa ggactttgca agatttatag tagggaactg   13740
ggagggcagc ctctagctta tgacgccata ctggcaatcg gcaaggtgct gctgctggaa   13800
tagatagtgg gccgctgatc cgagtttgat tttgtcgtat tatgttacgt gaactttta   13860 tcatgcatgt ttcgcttatg ctcccgagtg tcggccatgt tgttgtgtta aaataaaagg   13920
ctgatgttaa gtcctattgt aaaataccct tatagattaa atatatatag tataacttct   13980
gtatgccgtc gatgagcggt tatatgattg taatctatac gttgttgcaa tcaatcgtat   14040
tacagtgagc cgtgcttaat gaaataaaca tcatgttaaa tgtctattta ttcaatcaac   14100
atgcgctgac aataatcaaa aggggaaacg taataacatt gcggtggata cagcgtttat   14160
tgggaggtcc gcgggccgat acacttaaat aacatagaca gaatttgaga gagcacgcag   14220
gttgtagcca agttgagcga cttgccggta gcacggaagc taagctcagg tgttacaaat   14280
agacaggcgt cgaggcgacg agcacgacga ccttgccgga cattgcggtc caggggggct   14340
caaagcggtt ggcttgtaac ggaccttgtg tttcttgttg tagcttttcat cgagcataac   14400 cattgggacg gttgctgaac aacggtaacg cacttttttc acgggagcga ggtagaagaa   14460
catatttccc cgtcggcagc cggcggtgag catgccaatt cctaagggat caatggactc   14520
gtgcgaacgg tgagcatgcc gttctgaccg tcggtgccca atcagcaggc cactcccaac   14580
atgttttcca agtccttaaa accagtcttt atagcattga tctcccagca atctttattg   14640
aagtcgattt taatattcaa aagaagattt tagtggaaag ggaatataat cgcgtggccg   14700
aagaagagcc ttcaaaaatc agaatccact aggataaaca ataatatctg aaaagcattg   14760
aatttgggtt aggcacgaga ggctgacgcg gatgccactc gattgctagt ggaaggattc   14820
ccttttttct agcgtatcga attcaccgtt tcactatatg ttttcctgat tggttgatct   14880
gcgggaccac cattgactgc cactaatatc gaaagtgggt ctgcttcgat tatgatgctt   14940
tgtgagaggt tctcttccca atgcatgcaa gctggcagat tcggatactc tcaatagaga   15000
tcttatttcg cgtctcaaaa agttcccaga aatcaacaaa ggggagggca ggtcctttaa   15060
atacgttgca gctgtccttt aaaatagaag agaatttaca gctggaggca cagaccacta   15120
```

```
aactgcgaaa gtaagcatgg cagatgagtt ggagcgtcaa ttggaagcca tttctctcat   15180
tacagtcctg ggtccggatg tgaaggctga gcttgaggcg gagctacgag actactgcga   15240
agatctcgac ttctggaaaa gccacggttt accggtggcg gatctcgatc agactgtgac   15300
tgtcgacaag cttctataca tgtatatgga tcgggcaaca gcagacctgt gtgtgaagaa   15360
tcgctgcctc gtttgcaaca gtggcaattc agccgcaaaa gtaacctcgc ttccaccata   15420
ccttgcaggc gtgacaagcg ccgaggccta tgagaaactc aactccattg ttgatgggag   15480
tgtcgccccc caatctcgtg ggcctccctg ctattttgtg gcgttcctgc ccagcagctg   15540
tttcgagaaa accagtgaga tatcggtgcg cacagtggac ggcgagtgtg gcccctttga   15600
tgtctttacc cggcagcgtc agccacagga tcagagtgat atgttttttta aatatgaagg   15660 agttgtatgt gctggaaaga gtgtatttat gtaagaatta tcttttatag cctgtgttac   15720
gtttgaaccc ggtccgcgcg gtattgtttt caataaatgg tatgtgcgga ggatataatt   15780
ggtctttcat tggtgtgatt tacgtgtaac gcggataata ataaagtaaa ttacaaaaga   15840
gaaacgcata attttattcc agaatgattg cgagaaacga tgaaaataca tgaaaatgca   15900
tattgtcgcc agggaaggat ggcgccgaaa taaacgaaac tgagccaata cagtgacttg   15960
ccaagcgagt ttgatcctac caaattcgcg caaattaatg cccgtgttcc atcgggccag   16020
cgagtttatt caaaagagtt tcgtacacgt gggcggcgac ggcaacgtca atgcttgcta   16080
gccctaccgg cgagaagttg gccggccct tccatgcctt gaggtcattc atcaaggcct   16140
cgtcatcgag aatttcggtg tagttcttga tcccatcgcg cttgccgtgt tgggtcagtt   16200
tcataccgcg cctagaatag tagagggcaa cggcatcaac gttgcgggct tccatcgcaa   16260
caaggtcatc ggcgacaatt agaccatccg cagataggac atgctcaatg taatccggcg   16320
gcatgtcatc aataccgagt gacaaagtga ctgcgttggg ggcgatttca gcggcttcga   16380
ataccggttt tccgtagttg gtcgccatga tgacgaattg agaatatggc aaaaggctac   16440
gatcgccgac agcttcaagg ctaaaggtta cgcaatcacg taacttttcg acgagctcga   16500
aattggattt cttaccgcgg ctgagcactg ctaccttacg aattctctta gcggcaccat   16560
agttaagtga gagaattaca gcttcggcaa cttttccagc cccaaacaag aaaacgtcga   16620
tgtcctctct gccttgcaac agcaggttta cgcatgctag cgagaaccaa cccgttcttc   16680
cattagaaat tgccacgccc tctaccgaca taaggagcgt cccggacacc ttgtcgcgca   16740
ggaaaatatc ggagtgctgg agcggctttc cggtagcggc gttggttggc gcgaagtgga   16800
tgtctttggt gccggaatat cttccgaaat agccaatgag tgctccttca gtccatccag   16860
gaacattctt gttgaacgtt aggtaagctt tgacatgtcc ggcttttcct gcggcaaaca   16920
cctcccaata ggacttgaga gcttcgtcaa caaatgctgg tgtgatctgg atatcgaggt   16980
ttgatagtgc agattcagtc cagtgtacct cgcaaagttg tttggccatc tgccttgtag   17040
gtgcgaattt tctctgctca aattgttgag gttagcggat ttgtaaacgc gtttatatgg   17100
gctgcttgga gggtactttt ggattaattt ttttctgcca gcgcattctg acgcggcacc   17160
gctttggaaa gtgcgctgtg ggtccgcgtt ttctacaata atgtgccgat ccggtcagaa   17220
agtatatgga tgagttgtgc cagcctcacc aacgtgctgc aggcccatca tgactacttc   17280
aatgttaatg ggggtaatga ataaataggc gaaattgggt tcacggtggg cccagggaat   17340
ataatattgc cgcagaggta gtcggatgcc aaggcccgca actaatagtt cacgaacaaa   17400
ttcattgtag tgggcggcca actccaaaac caattgccag ttattgtatt gcaatacata   17460
```

-continued

```
tatgagtatt cggatacaac taatttcatt aaataatatt ttaagtgtgg acagaatagc   17520
gcctaataaa tttgcgaatg ttgtccaatt gacgttttta taggtaactc gataaatcgt   17580
gcttttgtga tattctgatg cggacaatat acatttaaac ataaagatat aagttattga   17640
ggcatttatg tatattacaa tagtggggta cattttttcac agatgctgtc acccatgaaa   17700
tattggcaaa atactcttaa aatatgcaag aaactaaaga ggatgcatgg gttgggctgt   17760
aggtacatgg atgcaaatgc tgttttgcaa taagtcatat agtctcgtct gttgagtgag   17820
gcccattcaa tcagcaagta ggactgaggt gcatgatcga catatttttg aaccacagtt   17880
ttggcaagtt tttcatacaa atgcacggct acggccaaat cgtagcttgc aagtccaact   17940
gctgaaaagt tagccggccc gttccaagaa attagccttt gcataaggac tggatcgcgg   18000
agaacttcag agtagttcct gatcccattg tccctgccgt gttttgttag ctttaaatgg   18060
cgtcttgaat agtgcagcgc caacgagtcg atattacgtg tttccatcgc atccatatca   18120
tctgccacca cgatgccact cagcttcaac acgtgatcaa aatagtcagc tgcaattcg    18180 tcaattccaa gcgtcaatgt aacggcattg tctgtgatct ccttcatctc aaagacgggc   18240
ttgtttgaat tcgtcgccgt aattatgaac ttggatttgc tgagatatgc tcgattgtta   18300
acagccttga gtgaaatctt gacttccggc tgaagccttt gcaccaactc atggtttgac   18360
tggttgcagc ggctgagaat cgcgattcgt tgaattcttc cagatgctcc cgaattgagg   18420
gcgaggatga tggcctcggc aactttacct gctccgaata ggaagacatt gatctggctt   18480
cggccctgca ataggagatt caggcatgct agtgccagcc aaccagttct cctctccgat   18540
atagccaccc catcaacaga gaagagacgt ctacctgtga aacgattgcg aagccaacgt   18600
cgatgtgaga agtcggttct ttgtatctcg cgtttgacgg attagaatgg atgcttttca   18660
cacccgaata gtcgccgacg aaacccacca gagctccctc cgtacagccc tctcgatcaa   18720
gtggaacgaa gaccttgttg tggccgagcc gcccttcagc aaagaggtgc aataatcttt   18780
tcaaggcatc cgcgacgagt tccggtgtaa tgtatattcc aaaagccgat agagattcct   18840
ctgtccaaca ttgctcgtgt atttgatcgg ccatgtttgt gtttgatcag cctccttttcg   18900 aaaatttctt gagtttcgaa taattctaaa atcgaaggac gattaatagt gccataccaa   18960
gacaagaagg gtaggtgggc catcaatcca caagcctagc acattttgct gtctgctcat    19020
gcaaggtatc caatggaagc ctggattggt tagccgaact tggtgggttc aattggagcg   19080
ggcaggtcac tttttgtctc tcaaataact gaaactaagt tttgttattt ggtatgtgtt   19140
tgtctgttct gccgaaggtg cccgaatttg cgcaaattcc tttctaaaaa ggcttacatc   19200
tagcaaaagg tgagccctgt gcatcccagc atttggacaa agcgcgccaa ttcggacagc   19260
gactggctgc gttggaggct cggatctcaa agaatagaaa agagttatga tcatgttcag   19320
aaccgccaat tttgtgcggt atgagctctt tgatgaaagt aatggtttca aaaaagcaac   19380
atcgtgggtg aaaggtacct acatatcttc acagacaata actactgttg ctgtttgctg   19440
attgactgac aggatatatg ttcctgtcat g                                   19471
```

<210> SEQ ID NO 2
<211> LENGTH: 5995
<212> TYPE: DNA
<213> ORGANISM: Agrobacterium rhizogenes

<400> SEQUENCE: 2

```
gtcgacagtc gcaacagcaa tcgaggggtg ttgatcaacc ttggccagtt gcccttcgtc     60
cctatcagta acgacaacct tgtaatcgcc ggtttccgca agcatcagag caatggctcc    120
```

```
gccaatctta cccgcgccga taaccactat ttctttcata caaatcccct gtgttctgta      180
tataggatat ttataaaaat aaccggggat tggtcgaatc atagcggcaa ggtgggcatt      240
atgttatata tttttgtgca aaaagacgac tgcacttggt aatatgaagg ggttccgcat      300
gcaattgacc gaaagggatc gggagctcct gtcgttactc ggcgaaaatg ccagaacgcc      360
tgtggcgacg ctcgcgaaaa agctttctct atccaggacc acagtgcagg ctcgcttgga      420
gcgccttgag agagagggag ttattgtcgg ctatggtgta aggctatcga atgaatattc      480
ctcgagcttg gttcgagccc atattctgat caccattacg aaggcgcttt cacaggtgac      540 ggcctcccctt gggaaggtca cggccgttat cgctcttcat tctgtgagtg cacttttga      600 tttgattgcg attatcgaag cccttcgat ttcagagctc gatcagttca tcgatcaaat      660
cggcataatt gaaggtgtcg agcggacgct ctcttcgatt attctttcaa cacgcatttc      720
acgctgaaag agcaagaggc cacagccgtg cgcctgctgc cacctttccg acgatgacca      780
tgcagaactt acgcctcta tgtcggtgta ttccacccac cgacgcgcca tttccgtgtg      840
cattaagata atgctttccg ccccatcgga ttgctgttct gacatggtat atcattacga      900
cagccaatgt ttggcggctc gtacgaatca tcaagcggtc aacctgtgct gtcaaccgtc      960
acgatatgag caagcaactc aaacgctttc ctattcaccg cacgcgcgtt gttggctgtt     1020
tggcaggata tatgccaacg taaaaatgag ggcaatcgat tgtactgaat cggatttcta     1080
agggtctggc caaaactatt ccgtgggcac ctggcacacg ccctggagtc cggcccgttt     1140
ccagttgagg gttgtctacg cttagatgag aaggaaagtt gtccaagacg aatcccagtg     1200
tcctattacc aatagccggc gctagttga tttcagaata aagagaaatt cgtcacacca     1260
aatattagaa gcaatgtttg attgaccatc atacttaaga tgaacattcc aaacacagtt     1320
ataatacgca ttattattga cacaatataa aattataatg ttgatattcc ttgaaatata     1380
atattacaat agataaagta gaggaaatta tgtcagaaat ttggtttggc tctgcttacg     1440
acagagtcgg acgatgccta aagtctattg cttcttctat cgctagtcca attgctaaca     1500
gacgttcatc cgagcttgca gagccatcga tttccatgcc aataggcaga ccgttggaac     1560
taagagaaac gggaagactt aggcccggca ggcccgcatt actgctggga tctacattcc     1620
gcacgaagat tttaaaggta tcggtcattg agccattgtg aatcaccgat agatcatggc     1680
caattggctt ggctgtcaac ggagctgttg ggaaaagaat tgcatctagc tgatgcgcct     1740
tgaagtaact gtggtaggcc gcttggagtc tcggtctgaa aaacgtcgc gccagacaat     1800 actcgctttt ggaaataaga ttatccgaga gttgtgcatt gagaatactt gcaacatccg     1860
gactgcgaat cgctctgaca acctcagaaa aggaaacacc ctctacgaag ttctgaatat     1920
aatgttcaag ggacaacgga aattcgtaga tggcagtcgg aaagctgacc ccttcattgt     1980
gatgcgctaa atcaggaata tctgcttcaa caaaagtaac atctttgcgt gccagaactc     2040
tgataatcgt ctcggctgct aaggcgacat cgggctccag gtcgttgtaa agtaagcgg     2100 ttggcaagcc tatacgcagc cccttcaggc ggaccgtttg attaaccggc ggtctcccgc     2160
aaatgatacc gtcaagaaga atcacgtccg gaacattctg tgcgataacg ccaggggtgt     2220
cccgggtggg gcttaccgga actattccgt ccgttggata tcgccccacg gtaggacgaa     2280
accccaccac gccgcacaag gcggccggta aacggaccga cgctcccgtg tcagttccga     2340
cgccgcccag catcaatcgg ccggccaccg cggcggccac cccccactt gatcccctg     2400 ggatgagact agggttccac gggtttcgta cggcgcctgt ggcgaagttg ttgctcgtga     2460
```

```
tcccaaaaga caattcgtgc atgtttcccg aagcgccagg cagtgcccca gccgcgagaa    2520
gttgtcgtgc aactccggca ggcgtcttgg gtttgtggtt ctgtaagcct ggcgtaccag    2580
cggtcgcggc gaacctgcct gtcgcaatat tcgctttaaa gcataggga acgccagcta    2640 ggccaacacc ggcacctccg tgttgatcga ttttgctggc agtccaccgt aggtgcgccc    2700
agtcggtttc cagaaaggcg tttaaggatc ttgctgcttc acagcgggct attatcgttt    2760
cgattaactc aaagcacgag tattttcttt ccctgagaca tttaagcgtc tcggtgatcg    2820
aggagagggt caccatttc gttgtgctga gggaactgag atagatctcg ccagagaaac    2880
gttcaatgat ttttgcttgg agtgaaaaag gcaaataatt atagaggaag gaagtcagaa    2940
atgctgcgca gtagggccac ttgtataagt gccggtcgaa cactgctggt ggaaagtcaa    3000
aagcgtgaag tattagttga actctgttac taaattgaga taaatgggat attttattcg    3060
aaagtactgt ttgagatcta gcgacaataa taatgtcatc ttatgagatt gcatggcaat    3120
atggatctaa tatttggcat aaatagatgg tggttttgtc tccacttttta aaccttcaca    3180 gcgttaccct aacacctctt aattgcgtac actcctttca accgcatcaa tggctggatc    3240
ctccttcaca ttgccatcaa ctggctcagc gcccctttgat atgatgctta tcgatgattc    3300
agatctgctg caattgggtc tccagcaggt attctcgaag cggtacacag agacaccgca    3360
gtcacgctac aaactgacca ggagggcttc tccagacgtc tcatctggcg aaggcaatgt    3420
gcatgccctt gcgttcatat atgtcaacgc tgagacgttg cagatgatca aaaacgctcg    3480
atcgctaacc gaagcgaacg gcgtcaaaga tcttgtcgcc atcgacgttc cgccatttcg    3540
aaacgacttc tcaagagcgc tactccttca agtgatcaac ttgttgggaa acaaccgaaa    3600
tgccgatgac gatcttagtc acttcatagc agttgctctc ccaaacagcg cccgctctaa    3660
gatcctaacc acggcaccgt tcgaaggaag cttgtcagaa aacttcaggg ggttcccgat    3720
cactcgtgaa ggaaatgtgg catgtgaagt gctagcctat gggaataact tgatgcccaa    3780
ggcctgctcc gattcctttc caaccgtgga tcttcttat gactatggca agttcttcga    3840
gagttgcgcg gccgatggac gtatcggtta ttttcctgaa ggcgttacga aacctaaagt    3900
ggctataatt ggcgcaggct tttccgggct cgttgcagcg agcgaactac ttcatgcagg    3960
ggtagacgat gttacggtgt atgaggcgag tgatcggctt ggaggaaagc tatggtcaca    4020
cggatttaag agtgctccaa atgtgatagc cgagatgggg gccatgcgtt ttccgcgaag    4080
tgaatcatgc ttgttcttct atctcaaaaa gcacggactg gactccgttg gtctgttccc    4140
gaatccggga agtgtcgata ccgcattgtt ctacaggggc cgtcaatata tctggaaagc    4200
gggagaggag ccaccggagc tgtttcgtcg tgtgcaccat ggatggcgcg cattttttgca    4260 agatggctat ctccatgatg gagtcatgtt ggcgtcaccg ttagcaattg ttgacgcctt    4320
gaatttaggg catctacagc aggcgcatgg cttctggcaa tcttggctca catattttga    4380
gcgagagtct ttctcttctg gcatcgaaaa aatgttcttg gcaatcatc ctccgggggg    4440 tgaacaatgg aattccctag atgacttgga tcttttcaaa gcgctgggta ttggatccgg    4500
cggattcggc cctgtatttg aaagtgggtt tatcgagatc cttcgcttag tcgtcaacgg    4560
gtatgaggat aacgtgcggc tgagttacga aggaatttct gagctgcctc ataggatcgc    4620
ctcacaggta attaacggca gatctattcg cgagcgtaca attcacgttc aagtcgagca    4680
gattgataga gaggaggata aaataaatat caagatcaaa ggaggaaagg ttgaggtcta    4740
tgatcgagta ctggttacat ccgggttgc gaacatcgaa atgcgccatc tcctgacatc    4800
aagcaacgca ttcttccatg cagatgtaag ccatgcaata gggaacagtc atatgactgg    4860
```

```
tgcgtcaaaa ctgttcttgc tgactaacga aaaattctgg ctacaacatc atttgccatc    4920
gtgcatactc accaccggcg ttgcaaaggc agtttattgc ttagactatg atccgcgaga    4980
tccaagcggc aaaggactgg tgttgataag ctatacttgg gaggatgact cacataagct    5040
cctagccgtc cccgacaaaa gagaaaggtt cgcatcgctg cagcgcgata ttgggagggc    5100
attcccagat tttgccaagc acctaactcc tgcagacggg aactatgatg ataatatcgt    5160
tcaacatgat tggctgactg atccccacgc tggcggagcg tttaaactga accgcagagg    5220
caacgacgta tattcagaaa ggcttttctt tcagcccttt gacgtaatgc atcccgcgga    5280
cgataaggga ctttacttgg ccggttgtag ctgttccttc accggagggt gggttcatgg    5340
tgccattcag accgcatgca acgctacgtg tgcgatcatt tatggttccg acacctgca     5400 agagctaatc cactggcgac acctcaaaga aggtaatcca ctggcgcacg cttggaagcg    5460
gtataggtat caagcgtgat aatgcaacag ttagaataat tagtttgccc tagccggtat    5520
tccttggtgt tccaataggg ttccgaagcc aataggcgaa aaagctgact tttcagtccc    5580
ttttattatt caattcgctt cggtccaagc ataattgtaa cgctacgtga tagaaaaatg    5640
gaaattgaca gattacttac ttaaattaat ataatctatt aatatcgtca agctaaaaac    5700
atgtaatacg taaatatatg gaactttat gtctgaaaag accacattat tattgatcgt     5760
aatacactga actggtcata acagggaagg ctaactgcaa catatcctat aaatactcag    5820
tgaaaatggc cgctccccaa tgttaagcca ttttttgcggt cgggctaagc gctcgtccgt    5880
gtctcccctg gcccgagtgt cggctctcca tcagcggcct catcatctgt cgctgacacc    5940
ggtggcccca atttcaaatc gaggaaagac gatgccctcg ccggcaaacg tcgac         5995

<210> SEQ ID NO 3
<211> LENGTH: 303
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggaattag ccggactaaa cgtcgccggc atggcccaga ccttcggagt attatcgctc      60
gtctgttcta agcttgttag gcgtgcaaag gccaagagga aggccaaacg ggtatccccg     120
ggcgaacgcg accatcttgc tgagccagcc aatctgagca ccactccttt ggccatgact    180
tcccaagccc gaccgggacg ttcaacgacc cgcgagttgc tgcgaaggga ccctttgtcg    240
ccggacgtga aaattcagac ctacgggatt aatacgcatt tcgaaacaaa cctacgggat    300
taa                                                                 303

<210> SEQ ID NO 4
<211> LENGTH: 780
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atggatccca aattgctatt ccttccacga tttcaaccag tagatctcac tccagcatgg     60
agccagataa acctattcga ggggatccga tttgcttttg caatctatag ccgtgactat    120
agcaaacccc tcctgcattt ccagaaacga tgggctcttg cagtgctaga tttgaaggaa    180
```

```
aactctccac cgatatatat acttaaacaa ctagctgagc tcttgaagaa caaagtctgc    240
tatcatcctc ctatgtttgt tagtcagccg gatctggctc gagaaaacga ccaacatgta    300
tttgtctatc tttctcgcga gaagatgcag aaagtgctga aggaacaatc cattacattt    360
ggaatggagg ccgtgctggc gacaacgatt caaccatatc ggagcgagct cgccctccag    420
gagatgctcc gtgttcacaa ccttgcttgg ccgcacagcc gcacggagga acctgattta    480
gaatgcttca tcgccatttt cgcaagttcc ttgttcattc acttgctgga gttaaaagtg    540
accaacgttt acgggagaga ggtagcttgc accttctttc tgcggcgagg gactgaaaac    600 cgccccctatg atgttgtagc ttgcggcacc acacaattca ccaaaaatgc cctcgggata    660
tcacgtccgg ccgcctcctc accggagcca gacctaaccc tgcgactctc ggggcctgat    720
caggaaggcg aggagggcgt catgaagcct gctgcagtaa acctgaagaa agaagcctaa    780
```

<210> SEQ ID NO 5
<211> LENGTH: 543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
atggctgaag acgacctgtg ttctctcttt ttcaagctca aagtggagga tgtgacaagc     60
agcgatgagc tagctagaca catgaagaac gcctcaaatg agcgtaaacc cttgatcgag    120
ccgggtgaga atcaatcgat ggatattgac gaagaaggag ggtcggtggg ccacgggctg    180
ctgtacctct acgtcgactg cccgacgatg atgctctgct tctatggagg gtccttgcct    240
tacaattgga tgcaaggcgc actcctcacc aaccttcccc cgtaccagca tgatgtgact    300
ctcgatgagg tcaatagagg gctcaggcaa gcatcaggtt ttttcggtta cgcggatcct    360
atgcggagcg cctacttcgc tgcatttttct ttccctgggc gtgtcatcaa gctgaatgag    420
cagatggagc taacttcgac aaagggaaag tgtctgacat cgacctcta tgccagcacc    480 cagcttaggt tcgaacctgg tgagttggtg aggcatggcg agtgcaagtt tgcaatcggc    540
taa                                                                 543
```

<210> SEQ ID NO 6
<211> LENGTH: 603
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atggctcgtt attgcagtgg tggctctcaa cggcttcatg tcgatgattt tcgttggatc     60
aaggagccca ctcgactgaa ggctcagctt attaatgtgg tggagaccta caaggctgca    120
caaacagaga cgttaaagta ctatatatca tctgcaactg agcgtgtggc tcatgtggag    180
gcagccgagg tcaacaatgc ggaaatggag ctgcatcctg ctgggttgaa gtaccctctg    240
tccttcgtct ttacctccct ggccgtggct acagcctgca aggagaacaa gcatctcttg    300
tgcgaggagc atttggaggg ggacttgata tcgtgcgtcg ttcctcccta tcagacaaat    360
gtctcactcg ctgctttaag ggagctccac aattccattt cgggaggagg gtaccaggaa    420
caagcagaca tggattattt tgtggcgatc atcccaaatg ataatttcga ctatcagagc    480
tgcgaaatcg acacacgaag ttgcggtaaa ggactttgca agatttatag tagggaactg    540
```

| | | | |
|---|---|---|---|
| ggagggcagc | tctagctta tgacgccata ctggcaatcg gcaaggtgct gctgctggaa | 600 |
| tag | | 603 |

<210> SEQ ID NO 7
<211> LENGTH: 2250
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 7

| | |
|---|---|
| atggctggat cctccttcac attgccatca actggctcag cgccccttga tatgatgctt | 60 |
| atcgatgatt cagatctgct gcaattgggt ctccagcagg tattctcgaa gcggtacaca | 120 |
| gagacaccgc agtcacgcta caaactgacc aggagggctt ctccagacgt ctcatctggc | 180 |
| gaaggcaatg tgcatgccct tgcgttcata tatgtcaacg ctgagacgtt gcagatgatc | 240 |
| aaaaacgctc gatcgctaac cgaagcgaac ggcgtcaaag atcttgtcgc catcgacgtt | 300 |
| ccgccatttc gaaacgactt ctcaagagcg ctactccttc aagtgatcaa cttgttggga | 360 |
| aacaaccgaa atgccgatga cgatcttagt cacttcatag cagttgctct cccaaacagc | 420 |
| gcccgctcta agatcctaac cacggcaccg ttcgaaggaa gcttgtcaga aaacttcagg | 480 |
| gggttcccga tcactcgtga aggaaatgtg gcatgtgaag tgctagccta tgggaataac | 540 |
| ttgatgccca aggcctgctc cgattccttt ccaaccgtgg atcttcttta tgactatggc | 600 |
| aagttcttcg agagttgcgc ggccgatgga cgtatcggtt attttcctga aggcgttacg | 660 |
| aaacctaaag tggctataat tggcgcaggc ttttccgggc tcgttgcagc gagcgaacta | 720 |
| cttcatgcag gggtagacga tgttacggtg tatgaggcga gtgatcggct tggaggaaag | 780 |
| ctatggtcac acggatttaa gagtgctcca aatgtgatag ccgagatggg ggccatgcgt | 840 |
| tttccgcgaa gtgaatcatg cttgttcttc tatctcaaaa agcacggact ggactccgtt | 900 |
| ggtctgttcc gaatccggg aagtgtcgat accgcattgt tctacagggg ccgtcaatat | 960 |
| atctggaaag cgggagagga gccaccggag ctgtttcgtc gtgtgcacca tggatggcgc | 1020 |
| gcatttttgc aagatggcta tctccatgat ggagtcatgt tggcgtcacc gttagcaatt | 1080 |
| gttgacgcct tgaatttagg gcatctacag caggcgcatg gcttctggca atcttggctc | 1140 |
| acatattttg agcgagagtc tttctcttct ggcatcgaaa aaatgttctt gggcaatcat | 1200 |
| cctccggggg gtgaacaatg gaattcccta tgacttggg atcttttcaa agcgctgggt | 1260 |
| attggatccg gcggattcgg ccctgtattt gaaagtgggt ttatcgagat ccttcgctta | 1320 |
| gtcgtcaacg ggtatgagga taacgtgcgg ctgagttacg aaggaatttc tgagctgcct | 1380 |
| cataggatcg cctcacaggt aattaacggc agatctattc gcgagcgtac aattcacgtt | 1440 |
| caagtcgagc agattgatag agaggaggat aaaataaata tcaagatcaa aggaggaaag | 1500 |
| gttgaggtct atgatcgagt actggttaca tccgggtttg cgaacatcga aatgcgccat | 1560 |
| ctcctgacat caagcaacgc attcttccat gcagatgtaa gccatgcaat agggaacagt | 1620 |
| catatgactg tgcgtcaaa actgttcttg ctgactaacg aaaaattctg gctacaacat | 1680 |
| catttgccat cgtgcatact caccaccggc gttgcaaagg cagtttattg cttagactat | 1740 |
| gatccgcgag atccaagcgg caaaggactg tgttgataa gctatacttg ggaggatgac | 1800 |
| tcacataagc tcctagccgt ccccgacaaa agagaaaggt tcgcatcgct gcagcgcgat | 1860 |
| attgggaggg cattcccaga ttttgccaag cacctaactc ctgcagacgg gaactatgat | 1920 |

```
gataatatcg ttcaacatga ttggctgact gatccccacg ctggcggagc gtttaaactg    1980
aaccgcagag gcaacgacgt atattcagaa aggcttttct ttcagccctt tgacgtaatg    2040
catcccgcgg acgataaggg actttacttg gccggttgta gctgttcctt caccggaggg    2100
tgggttcatg gtgccattca gaccgcatgc aacgctacgt gtgcgatcat ttatggttcc    2160
ggacacctgc aagagctaat ccactggcga cacctcaaag aaggtaatcc actggcgcac    2220
gcttggaagc ggtataggta tcaagcgtga                                     2250

<210> SEQ ID NO 8
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atggtgaccc tctcctcgat caccgagacg cttaaatgtc tcagggaaag aaaatactcg     60
tgctttgagt taatcgaaac gataatagcc cgctgtgaag cagcaagatc cttaaacgcc    120
tttctggaaa ccgactgggc gcacctacgt tggactgcca gcaaaatcga tcaacacgga    180
ggtgccggtg ttggcctagc tggcgttccc ctatgcttta aagcgaatat tgcgacaggc    240
aggttcgccg cgaccgctgg tacgccaggc ttacagaacc acaaaccaa gacgcctgcc     300 ggagttgcac gacaacttct cgcggctggg gcactgcctg gcgcttcggg aaacatgcac    360
gaattgtctt ttgggatcac gagcaacaac ttcgccacag gcgccgtacg aaacccgtgg    420
aaccctagtc tcatcccagg gggatcaagt gggggtgtgg ccgccgcggt ggccggccga    480
ttgatgctgg gcgcgtcgg aactgacacg ggagcgtcgg tccgtttacc ggccgccttg    540
tgcggcgtgg tggggtttcg tcctaccgtg gggcgatatc caacggacgg aatagttccg    600
gtaagcccca cccgggacac ccctggcgtt atcgcacaga atgttccgga cgtgattctt    660
cttgacggta tcatttgcgg gagaccgccg gttaatcaaa cggtccgcct gaaggggctg    720
cgtataggct tgccaaccgc ttactttac aacgacctgg agcccgatgt cgccttagca     780
gccgagacga ttatcagagt tctggcacgc aaagatgtta cttttgttga agcagatatt    840
cctgatttag cgcatcacaa tgaaggggtc agctttccga ctgccatcta cgaatttccg    900
ttgtcccttg aacattatat tcagaacttc gtagagggtg tttccttttc tgaggttgtc    960
agagcgattc gcagtccgga tgttgcaagt attctcaatg cacaactctc ggataatctt    1020
atttccaaaa gcgagtattg tctggcgcga cgttttttca gaccgagact ccaagcggcc    1080
taccacagtt acttcaaggc gcatcagcta gatgcaattc ttttcccaac agctccgttg    1140
acagccaagc caattggcca tgatctatcg gtgattcaca atggctcaat gaccgatacc    1200
tttaaaatct tcgtgcggaa tgtagatccc agcagtaatg cgggcctgcc gggcctaagt    1260
cttcccgttt ctcttagttc caacggtctg cctattggca tggaaatcga tggctctgca    1320
agctcggatg aacgtctgtt agcaattgga ctagcgatag aagaagcaat agactttagg    1380
catcgtccga ctctgtcgta a                                              1401

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                          primer

<400> SEQUENCE: 9
caatagaggg ctcaggcaag                                                   20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cctcaccaac tcaccaggtt                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aatgagggct tgttggatga                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttgagtgat ggctccttcc                                                   20
```

PLANTS COMPRISING A LOW COPY NUMBER OF RI GENES

The present invention relates to a plant, transformed with one or more genes originating from the Ri plasmid of *Agrobacterium rhizogenes* by infection with *A. rhizogenes* harbouring the Ri plasmid, or being progeny of such a plant, in particular having intermediate height and to methods for the preparation thereof.

Compact plant architecture is more and more desired in the field of ornamental plants. The potted plant industry favors more compact plant architecture for environmental, space and transportation purposes. Potted plants displaying an elongated growth behavior are losing interest of both the breeders, plant producers and the consumers.

At present, the industry treats plants with growth retardants to limit plant size. Further, plants transformed with *Agrobacterium rhizogenes* having compact plant architecture where the length of the transformed plants is less than 20% of the height of the untransformed wild type plant. Such transformants display numerous phenotypes, including dwarfism and compact plants growth. Said compact growth coincided with undesired phenotypes, such as wrinkled leaves, flower shape, reduced flower number, delayed flowering. For ornamental plants, the disadvantages of the *Agrobacterium rhizogenes* transfection appeared to be larger than the envisaged advantages of compact growth. The compact growth often results in plants that are too small to have commercial value. Although transformants are occasionally observed that are less affected in plant height, such transformants suffer from the other undersired phenotypes.

Indeed, Christensen et al. (Plant Cell Rep (2008) 27, 1485-1495) describe transformation of *Kalanchoe blossfeldiana* with rol genes of *A. rhizogenes* by infection with *A. rhizogenes* harbouring the Ri plasmid. Different Ri lines were obtained, varying in length and compactness. However, all plants suffered from wrinkled leaves, smaller flower size, decreased dry weight, a severe reduction of flower number by at least 50% and a delayed flowering time. By Southern blot analysis, some of the Ri-lines were described to have 1 (lines 306 and 319) or two copies (line 331) of the Ri plasmid, whereas other lines (312 and 324) showed multiple bands in the Southern blot. These data however, are unreliable and appear to be wrong. A first indication of the estimation of Christensen being wrong lies in the fact that the Ri-lines of Christensen were the result of straight transformation of *Kalanchoe blossfeldiana* with *A. rhizogenes*, which results in incorporation of multiple Ri copies in the Kalanchoe genome. The number varies between 7 and 11 or even more, but never less. Further, the Ri-lines of Christensen suffer from a dramatic decrease in inflorescences, flower number and dry weigh loss. A significantly more reliable method to determine the copy number, qPCR as used herein, indeed showed that the copy number line 331 of Christensen was 7. Further, the phenotypes observed by Christensen do not seem to coincide with the alleged copy number; e.g. leaf wrinkling seems to be less pronounced in lines 306 and 331, while the copy number of the rol genes is said to be double in line 331 as compared to line 306, whereas line 319, said to have the same copy number as line 306, has more pronounced wrinkled leaves than both lines 331 and 306. Also, the delayed flowering is less pronounced in line 331 as compared to counterparts said to comprise less copies of the rol genes.

The Ri-plasmid of naturally occurring soil bacterium *A. rhizogenes* agropine-type strains carry two T-DNA regions ($T_L$-DNA and $T_R$-DNA, SEQ ID NO 1 and 2, respectively) on the Ri-plasmid for transfer into plant cells. Following infection of a plant cell, the bacterium transfers the entire T-DNA region (both $T_L$-DNA and $T_R$-DNA), thereby transferring rol (root loci) and aux genes into the plant genome and causing hairy root growth at the site of infection (Tepfer (1984) Cell, 37, pp. 959-967). Because *A. rhizogenes* naturally infects plants, the rol genes are naturally transferred into the plant and function as plant oncogenes and develop hairy roots in plant tissues.

The $T_L$-DNA contains four rol genes, rolA, rolB, rolC, and rolD (SEQ ID Nos 3-6, respectively), whereas the $T_R$-DNA contains several genes, including two auxin genes, aux1 and aux2 (SEQ ID Nos 7 and 8, respectively). $T_L$-DNA comprises further 18 open reading frames (Veena and Taylor (2007), In Vitro Cellular & Developmental Biology—Plant, 43, 383-403).

Terminology

All technical terms used herein are terms commonly used in biochemistry, molecular biology and agriculture, and can be understood by one of ordinary skill in the art. Technical terms can be found in: Molecular Cloning: A Laboratory Manual, 3rd ed., vol. 1-3, ed. Sambrook and Russell, Cold Spring Harbor Laboratory Press, Cold Spring Harbor, N.Y., 2001; Current Protocols in Molecular Biology, ed. Ausubel et al., Greene Publishing Associates and Wiley-Interscience, New York, 1988 (with periodic updates); Short Protocols in Molecular Biology: A Compendium of Methods from Current Protocols in Molecular Biology, 5th ed., vol. 1-2, ed. Ausubel et al., John Wiley & Sons, Inc., 2002; Genome Analysis: A Laboratory Manual, vol. 1-2, ed. Green et al., Cold Spring Harbor Laboratory Press, Cold Spring Harbor, N.Y., 1997. Methodology involving plant biology techniques is described herein and is described in detail in treatises such as Methods in Plant Molecular Biology: A Laboratory Course Manual, ed. Maliga et al., Cold Spring Harbor Laboratory Press, Cold Spring Harbor, N.Y., 1995. Various techniques using PCR are described in Innis et al., PCR Protocols: A Guide to Methods and Applications, Academic Press, San Diego, 1990 and in Dieffenbach and Dveksler, PCR Primer: A Laboratory Manual, 2nd ed., Cold Spring Harbor Laboratory Press, Cold Spring Harbor, N.Y., 2003. PCR-primer pairs can be derived from known sequences by known techniques such as using computer programs intended for that purpose, Primer, Version 0.5, 1991, Whitehead Institute for Biomedical Research, Cambridge, Mass. Methods for chemical synthesis of nucleic acids are discussed, for example, in Beaucage and Caruthers, 1981, Tetra. Letts. 22: 1859-1862, and Matteucci and Caruthers, 1981 J. Am. Chem. Soc. 103: 3185. Restriction enzyme digestions, phosphorylations, ligations and transformations were done as described in Sambrook et al., Molecular Cloning: A Laboratory Manual, 2nd ed. (1989), Cold Spring Harbor Laboratory Press. All reagents and materials used for the growth and maintenance of bacterial cells were obtained from Aldrich Chemicals (Milwaukee, Wis.), DIFCO Laboratories (Detroit, Mich.), Invitrogen (Gaithersburg, Md.), or Sigma Chemical Company (St. Louis, Mo.), unless otherwise specified.

"Transformation" refers herein to any methodology for introducing one or more genes originating from a Ri plasmid of *Agrobacterium rhizogenes* into a host plant cell. In particular, said one or more gens comprise one or more rol genes. Importantly, and because *A. rhizogenes* naturally infects plants, transformation includes the natural transfer of wild-type genes from the Ri plasmid from the wild-type bacterium into a plant cell, in particular rol genes. Thus, and as used herein, transformation neither implies nor requires cloning a heterologous gene into a vector for transfer into a host plant cell. Furthermore, a host plant cell expressing one or more genes originating from a Ri plasmid of *Agrobacterium rhizogenes*, such as one or more rol genes may be characterized as "transformed." Transformation may occur by any known method including, for example, natural infection, floral dip, infiltration, or particle bombardment. Transformation of a cell may be detected by any known means, including but not limited to Northern Blot, Southern blot, PCR, RT-PCR (syn. q-PCR, qRT-PCR) and/or genomic sequencing. It is also possible to take one or more genes, originating from the Ri plasmid of *Agrobacterium tumefaciens* from the said plasmid, and use it outside the context of the *Agrobacterium tumefaciens* system to transform an envisaged plant. The skilled person will be aware of such methods.

The term "tissue culture" refers to plant tissues propagated under sterile conditions, often for producing clones of a plant. Plant tissue culture relies on the fact that many plant cells have the ability to regenerate a whole plant. Single cells, plant cells without cell walls (protoplasts), pieces of leaves, or roots can often be used to generate a new plant on culture media given the required nutrients and plant hormones.

As used herein, "interspecific hybrid" includes the progeny from the cross of two different species of plants of the same genus and its cultivars, as well as progeny resulting from subsequent backcrossing to one of the parents or siblings or cultivars from the same or compatible species. This backcrossing to one of the parents may be conducted one or more times with the goal of stably combining the compactsness trait with desired characteristics. "Interspecific hybrid" embraces any plant with an interspecific cross in its background. That is, interspecific hybrids include both the first and subsequent generations of crosses between two plant species, as well as the progeny produced from either selfing an interspecific hybrid or crossing an interspecific hybrid with a plant of the same or different species.

*A. rhizogenes* refers to *Agrobacterium rhizogenes* and its Ri-plasmid from an agropine strain. The T-DNA contains two segments, $T_L$ and $T_R$, which are separated by a 15 Kb sequence that is not integrated. The $T_L$-DNA contains 18 open reading frames (ORFs) where the four root loci-genes reside. The $T_R$-DNA contains several genes, including aux1 and aux2.

"Hairy root phenotype" refers to a plant phenotype indicative of a putative transformed plant. That is, when *A. rhizogenes* infects a plant cell and transfer one or more rol genes, hairy root growth occurs at the infection site. In this way, a hairy root phenotype offers a marker-free method for identifying putative transformants.

"Intermediate height" refers to a quantitative reduction of plant height relative to the height of a wild-type or control plant of the same species but to an increase in plant height relative to the height of a plant of the said species transformed with one or more genes of the Ri plasmid of *Agrobacterium rhizogenes*. As transformed plants often display compact growth or dwarfism, the height of a transformed plant is usually about by less than 20%, 15% or 10% of the height of a wild type non transformed control plant. So as compared to the height of a wild type untransformed plant of the same species, preferably a parent plant from which the transformed plant originates, plants of 'intermediate height' are defined by a height of 25%-75% of the height of the wild type untransformed plant, preferably of 30-70%, more preferably of 40-60%.

"Intermediate compactness" refers to a quantitative increase of plant compactness relative to a wild-type or control plant of the same species. Compactness correlates with the distance between the internodes. The shorter the internodes, the compacter the plant. Intermediate compactness is herein defined by a reduction in distance between the internodes of 25-75%, preferably of 30-70%, more preferably of 40-60%. The phrase "intermediate compactness" interrelates with "intermediate length". In Ri transformants, in particular rol transformants, compactness increases when length decreases.

The terms "control plant" and "wild type plant" are intended to mean a same plant as a transformant plant, i.e. originating from the same parental source or belonging to the same species or variety. The skilled person will immediately understand how to compare transformed plant with control or wild type plants and what plants to take as control plant, i.e. to check whether a transformation event has taken place.

The term "progeny" of a plant encompasses all offspring plants, that have the said plant as an ancestor.

A. Nucleic Acid Sequences

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene, particularly a fragment encoding at least a portion of a protein. The fragments may range in size from a few nucleotides to the entire gene sequence minus one nucleotide. Thus, "a nucleic acid sequence comprising at least a part of a gene" may comprise fragments of the gene or the entire gene. "Gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated (or untranslated) sequences (5' UTR). The sequences which are located 3' or downstream of the coding region and which are present on the mRNA are referred to as 3' non-translated (or untranslated) sequences (3' UTR).

"Nucleic acid" as used herein refers to RNA or DNA that is linear or branched, single or double stranded, or a hybrid thereof. The term also encompasses RNA/DNA hybrids.

"Encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein. It is therefore understood that modifications in the DNA sequence encoding transcription factors which do not substantially affect the functional properties of the protein are contemplated.

The term "expression," as used herein, refers to the production of a functional end-product e.g., an mRNA or a protein.

The terms "polypeptide," "peptide" and "protein" are used interchangeably herein to refer to a polymer of amino acid residues. The terms apply to amino acid polymers in which one or more amino acid residue is an artificial chemical analog of a corresponding naturally occurring amino acid, as well as to naturally occurring amino acid polymers. Probe or primer refers to a short oligonucleotide sequence that could be designed and synthesized, or generated as a fragment of a larger sequence. A probe or primer can be any length, such as 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length.

Illustrative rol sequences include but are not limited to the sequences set forth in SEQ ID NOs: 1-12, respectively, as well as nucleic acid molecules comprised of fragments or variants of SEQ ID NO: 1-12 with one or more bases deleted, substituted, inserted, or added, which variant codes for a polypeptide with rol activity. For example, and in no way limiting, the present disclosure provides SEQ ID NO: 1, as well as various fragments of SEQ ID NO: 1, which could include, for example, rolA-D and aux1-2. For instance, and as readily apparent to one of ordinary skill in the art, the rolA gene could represent a 700 bp portion or fragment of a larger sequence comprising rolA-D and aux1-2.

A "variant" is a nucleotide or amino acid sequence that deviates from the standard, or given, nucleotide or amino acid sequence of a particular gene or protein. The terms "isoform," "isotype," and "analog" also refer to "variant" forms of a nucleotide or an amino acid sequence. An amino acid sequence that is altered by the addition, removal, or substitution of one or more amino acids, or a change in nucleotide sequence, may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, Md.) software. "Variant" may also refer to a "shuffled gene" such as those described in Maxygen-assigned patents.

Included in the category of "variant" sequences are sequences that hybridize to a reference rol sequence. For example, two sequences hybridize when they form a double-stranded complex in a hybridization solution of 6× SSC, 0.5% SDS, 5×Denhardt's solution and 100 µg of non-specific carrier DNA. See Ausubel et al., supra, at section 2.9, supplement 27 (1994). Sequences may hybridize at "moderate stringency," which is defined as a temperature of 60.degree. C. in a hybridization solution of 6.times.SSC, 0.5% SDS, 5.times. Denhardt's solution and 100 .mu.g of non-specific carrier DNA. For "high stringency" hybridization, the temperature is increased to 68.degree. C. Following the moderate stringency hybridization reaction, the nucleotides are washed in a solution of 2.times.SSC plus 0.05% SDS for five times at room temperature, with subsequent washes with 0.1.times.SSC plus 0.1% SDS at 60.degree. C. for 1 hour. For high stringency, the wash temperature is increased to 68.degree. C. One with ordinary skill in the art can readily select such conditions by varying the temperature during the hybridization reaction and washing process, the salt concentration during the hybridization reaction and washing process, and so forth. For present purposes, hybridized nucleotides can be detected using 1 ng of a radiolabeled probe having a specific radioactivity of 10,000 cpm/ng, where the hybridized nucleotides are clearly visible following exposure to X-ray film at −70.degree. C. for no more than 72 hours.

The present application is directed to such nucleic acid molecules that are at least 60%, 65%, 70%, 75%, 80%, 85%, 90%, 95%, 96%, 97%, 98%, 99% % or 100% identical to a nucleic acid sequence described in any of SEQ ID NO: 1-18. Preferred are nucleic acid molecules which are at least 95%, 96%, 97%, 98%, 99% or 100% identical to the nucleic acid sequence shown in any of SEQ ID NO: 1-18. Differences between two nucleic acid sequences may occur at the 5' or 3' terminal positions of the reference nucleotide As a practical matter, stating whether any particular nucleic acid molecule is at least 95%, 96%, 97%, 98% or 99% identical to a reference nucleotide sequence implicates a comparison made between two molecules, using algorithms known in the art and can be determined conventionally using publicly available computer programs such as the BLASTN algorithm. See Altschul et al., Nucleic Acids Res. 25: 3389-402 (1997).

The terms "sequence identity" and "sequence similarity" can be determined by alignment of two peptide or two nucleotide sequences using global or local alignment algorithms. Sequences may then be referred to as "substantially identical" or "essentially similar" when they share at least 70% of sequence identity over their entire length, respectively. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or EmbossWin version 2.10.0 (using the program "needle"). Alternatively percent similarity or identity may be determined by searching against databases, using algorithm as FASTA, BLAST, etc.

The present disclosure may contemplate nucleic acid molecules encoding functional proteins. As known in the art, it is understood that such proteins encompass amino acid substitutions, additions, and deletions that do not alter the function of any of the proteins. Because many proteins are encoded by gene families, it is expected that other genes couldencode proteins with similar functions as the instant polypeptides. These genes can be identified and functionally annotated by sequence comparison. A worker skilled in the art can identify a functionally related protein sequence with the aid of conventional methods such as screening cDNA libraries or genomic libraries with suitable hybridization probes. The skilled artisan knows that paralogous sequences can also be isolated with the aid of (degenerate) oligonucleotides and PCR-based methods.

B. Nucleic Acid Constructs

As explained above, one or more gene sequences originating from a Ri plasmid of *Agrobacterium rhizogenes* are transferred into a host plant cell. Such transfer can occur through natural means, such as natural infection of plant cell with *A. rhizogenes* carrying the Ri plasmid including native rol genes. Such natural or native transfer avoids the need for constructs and selection markers.

However, in another aspect, one or more one or more genes originating from a Ri plasmid of *Agrobacterium rhizogenes*, including rol sequences can be incorporated into a nucleic acid construct that is suitable for introduction into a plant cell. Thus, in instance where a native system is not employed, a nucleic acid construct can be used to express rol in a plant cell.

Exemplary nucleic acid constructs may comprise a base sequence of a minimum length to generate a mRNA and consequently a polypeptide. There is no theoretical upper limit to the base sequence length. The preparation of such constructs is described in more detail below.

As a source of the nucleic acid sequence for transcription, a suitable cDNA or genomic DNA or synthetic polynucleotide may be used. Methods for the isolation of suitable rol sequences are described, supra. Sequences coding for the whole, or substantially the whole, of the sequence may thus be obtained. Suitable lengths of this DNA sequence may be cut out for use by means of restriction enzymes. When using genomic DNA as the source of a partial base sequence for transcription, it is possible to use either intron or exon regions or a combination of both.

Recombinant nucleic acid constructs may be made using standard techniques. For example, the nucleic acid sequence for transcription may be obtained by treating a vector containing said sequence with restriction enzymes to cut out the appropriate segment. The nucleic acid sequence for transcription may also be generated by annealing and ligating synthetic oligonucleotides or by using synthetic oligonucleotides in a polymerase chain reaction (PCR) to give suitable restriction sites at each end. The nucleic acid sequence then is cloned into a vector containing suitable regulatory elements, such as upstream promoter and downstream terminator sequences.

Another aspect concerns a nucleic acid construct wherein a gene sequence of one or more genes originating from a Ri plasmid of *Agrobacterium rhizogenes*, such as a rol sequence is operably linked to one or more regulatory sequences, which drive expression of the rol sequence in certain cell types, organs, or tissues without unduly affecting normal development or plant physiology.

Of course, and in the context of a natural transformation or natural infection system, native or endogenous regulatory sequences are used, rather than heterologous sequences.

"Promoter" connotes a region of DNA upstream from the start of transcription that is involved in recognition and binding of RNA polymerase and other proteins to initiate transcription. A "constitutive promoter" is one that is active throughout the life of the plant and under most environmental conditions. Tissue-specific, tissue-preferred, cell type-specific, and inducible promoters constitute the class of "non-constitutive promoters." "Operably linked" refers to a functional linkage between a promoter and a second sequence, where the promoter sequence initiates and mediates transcription of the DNA sequence corresponding to the second sequence. In general, "operably linked" means that the nucleic acid sequences being linked are contiguous.

Promoters useful for expression of a nucleic acid sequence introduced into a cell may include native or endogenous promoters for natural transformation systems, or constitutive promoters, such as the cauliflower mosaic virus (CaMV) 35S promoter, or tissue-specific, tissue-preferred, cell type-specific, and inducible promoters. For example, by using vascular system-specific, xylem-specific, or xylem-preferred promoters, one can modify rol expression specifically in many tissues such as vascular tissues, especially xylem. The use of a constitutive promoter in general affects enzyme levels and functions in all parts of the plant, while use of a tissue-preferred promoter permits targeting of the modified gene expression to specific plant parts, leading to a more controllable phenotypes.

A vector may also contain a termination sequence, positioned downstream of a rol sequence, such that transcription of mRNA is terminated, and polyA sequences added. Exemplary of such terminators are native or endogenous terminator sequenes, cauliflower mosaic virus (CaMV) 35S terminator, or the nopaline synthase gene (Tnos) terminator.

The expression vector also may contain enhancers, start codons, splicing signal sequences, and targeting sequences.

Expression vectors may also contain a selection marker by which transformed cells can be identified in culture. The marker may be associated with the heterologous nucleic acid molecule, i.e., the gene operably linked to a promoter. As used herein, the term "marker" refers to a gene encoding a trait or a phenotype that permits the selection of, or the screening for, a plant or cell containing the marker. In plants, for example, the marker gene will encode antibiotic or herbicide resistance. This allows for selection of transformed cells from among cells that are not transformed or transfected.

Examples of suitable selectable markers include adenosine deaminase, dihydrofolate reductase, hygromycin-B-phosphotransferase, thymidne kinase, xanthine-guanine phospho-ribosyltransferase, glyphosate and glufosinate resistance, and amino-glycoside 3'-O-phosphotranserase (kanamycin, neomycin and G418 resistance). These markers may include resistance to G418, hygromycin, bleomycin, kanamycin, and gentamicin. The construct may also contain the selectable marker gene Bar that confers resistance to herbicidal phosphinothricin analogs like ammonium gluphosinate. Thompson et al., EMBO J. 9: 2519-23 (1987). Other suitable selection markers are known as well.

Visible markers such as green florescent protein (GFP) may be used. Methods for identifying or selecting transformed plants based on the control of cell division have also been described. See WO 2000/052168 and WO 2001/059086. Likewise, the presence of a distinguishing phenotype, such as tumor or hairy root growth, may also be used for identification and selection.

In a natural transformation or natural infection system, a selection marker is not employed. Because infection provides its own distinct and natural phenotype, a transformed cell can be selected based on a post-infection phenotype, such as hairy root phenotype.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other nucleic acid sequences encoding additional functions may also be present in the vector, as is known in the art. For instance, when *Agrobacterium* is the host, T-DNA sequences may be included to facilitate the subsequent transfer to and incorporation into plant chromosomes.

C. Transformation Methodology: Transfer of Genes

As explained above, transformation" refers to any methodology for introducing one or more genes originating from *Agrobacterium rhizogenes* into a host plant or plant cell. Importantly, and because *A. rhizogenes* naturally infects plants, transformation embraces transferring wild-type genes from the Ri plasmid from wild-type bacterium into a plant cell, in particular one or more rol genes and/or aux genes. Thus, and as used herein, transformation does not require cloning a heterologous gene into a vector for transfer into a host plant cell, nor does transformation require genetically engineering the bacterium.

"Transformed plant" refers to a plant that comprises a nucleic acid sequence that also is present per se in another organism or species, or that is optimized, relative to host codon usage, from another organism or species. Both monocotyledonous and dicotyledonous angiosperm or gymnosperm plant cells may be transformed in various ways known to the art. For example, see Klein et al., *Biotechnology* 4: 583-590 (1993); Bechtold et al., C. R. *Acad. Sci. Paris* 316: 1194-1199 (1993); Bent et al., *Mol. Gen. Genet.* 204: 383-396 (1986); Paszowski et al., *EMBO J.* 3: 2717-2722 (1984); Sagi et al., Plant Cell Rep. 13: 262-266 (1994). *Agrobacterium* species such as *A. tumefaciens* and *A. rhizogenes* can be used, for example, in accordance with Nagel et al., *Microbiol Lett* 67: 325 (1990). Additionally, plants may be transformed by *Rhizobium, Sinorhizobium* or *Mesorhizobium* transformation. Broothaerts et al., *Nature* 433: 629-633 (2005).

For example, *Agrobacterium* may be transformed with a plant expression vector via, e.g., electroporation, after which the *Agrobacterium* is introduced to plant cells via, e.g., the well known leaf-disk method. Additional methods for accomplishing this include, but are not limited to, electroporation, particle gun bombardment, calcium phosphate precipitation, and polyethylene glycol fusion, transfer into germinating pollen grains, direct transformation, Lorz et al., *Mol. Genet.* 199: 179-182 (1985), and other methods known to the art. If a selection marker, such as kanamycin resistance, is employed, it makes it easier to determine which cells have been successfully transformed. Marker genes may be included within pairs of recombination sites recognized by specific recombinases such as cre or flp to facilitate removal of the marker after selection. See U.S. published application No. 2004/0143874.

Transgenic plants without marker genes may be produced using a second plasmid comprising a nucleic acid encoding the marker, distinct from a first plasmid that comprises a gene sequence originating from the *Agrobacterium rhizogenes* Ri plasmid, in particular a rol sequence. The first and second plasmids or portions thereof are introduced into the same plant cell, such that the selectable marker gene that is transiently expressed, transformed plant cells are identified, and transformed plants are obtained in which the envisaged gene sequence, such as a rol sequence is stably integrated into the genome and the selectable marker gene is not stably integrated. See U.S. published application No. 2003/0221213.

The *Agrobacterium* transformation methods discussed above are known for transforming dicots. Additionally, de la Pena et al., *Nature* 325: 274-276 (1987), Rhodes et al., *Science* 240: 204-207 (1988), and Shimamato et al., *Nature* 328: 274-276 (1989) have transformed cereal monocots using *Agrobacterium*. Also see Bechtold et al., C. R. Acad. Sci. Paris 316 (1994), illustrating vacuum infiltration for *Agrobacterium*-mediated transformation.

Plant cells may be transformed with a nucleic acid or nucleic acid construct without the use of a selectable or visible marker, and transgenic organisms may be identified by detecting the presence of the introduced sequence or construct. The presence of a protein, polypeptide, or nucleic acid molecule in a particular cell can be measured to determine if, for example, a cell has been successfully transformed or transfected. For example, and as routine in the art, the presence of the introduced construct can be detected by PCR or other suitable methods for detecting a specific nucleic acid or polypeptide sequence. Additionally, transformed cells may be identified by recognizing differences in the growth rate or a morphological feature of a transformed cell compared to the growth rate or a morphological feature of a non-transformed cell that is cultured under similar conditions. See WO 2004/076625.

Methods of regenerating a plant from a transformed cell or culture vary according to the plant species but are based on known methodology. For example, methods for regenerating Kalanchoe plants are well-known in the art can be found in Christensen, et al, (2008). *Plant Cell Rep.* 27, 1485-1495.

D. Selection and Analysis of Plants Transformed With *A.Rhizogenes*

The present transformed plants are selected that contain and express one or more genes originating from the Ri plasmid of *Agrobacterium rhizogenes* relative to a control, non-transformed plant of the same species, said genes preferably comprising one or more rol genes. Additionally, the instant plants may have an altered phenotype relative to a non-transformed control plant. Such phenotype may include an intermediate height or intermediate compactness, wherein the transformed plant has a reduced height and/or compactness relative to the control plant.

The present inventors have now, in a first aspect of the invention, surprisingly found plants, transformed with one or more genes originating from the Ri plasmid of *Agrobacterium rhizogenes* by infection with *A. rhizogenes* harbouring the Ri plasmid, not having the above disadvantages or to a significant lesser extent, but instead, display the envisaged intermediate growth, while not or at least not significantly being affected in the number of flowers and other undesired phenotypes such as wrinkles leaves. Herein, the phrase 'originating from *Agrobacterium rhizogenes*' is particularly intended to mean 'originating from the Ri plasmid of *Agrobacterium rhizogenes*', in particular from the $T_L$- and $T_R$-DNA of the Ri plasmid as shown in SEQ ID NOs 1 and 2, respectively. To this end, the invention provides a transformed plant with one or more genes originating from the Ri plasmid of *Agrobacterium rhizogenes* by infection with *A. rhizogenes* harbouring the Ri plasmid, or being progeny of such a plant, said plant or progeny comprising, in the genome thereof, 1 to 5 copies said one or more genes originating from the Ri pasmid. The plant of the invention is obtained by infection with *A. rhizogenes*, so that the genes that originate from the Ri plasmid are introduced in cells of the plant by introduction of the Ri plasmid therein. This means that the said genes are introduced in the plant cells in their natural environment, void of any DNA, not originating from the Ri plasmid. Therefore, the term "genes originating from the Ri plasmid" means that the host is transformed with the Ri pasmid, resulting in genes of the RI plasmid to become incorporated in the plant genome.

By infection of a plant with *A. rhizogenes* harbouring the Ri plasmid, the Ri plasmid is introduced in the plant cells. As indicated above, this event usually results in incorporation of multiple copies of the Ri plasmid, i.e. including all genes present thereon, in the plant genome. It has however been found that specific selection techniques, in particular with regard to characteristics of the hairy roots that develop as a result of the infection, or by crossing transformed plants with untransfected plants to dilute the number of genes originating from the Ri plasmid in the plant genome, results in plants with a limited number of genes originating from the Ri plasmid. It is also possible to obtain offspring of a plant, transformed with the Ri plasmid by *A. rhizogenes* infection, wherein one or more of the genes originating from the Ri plasmid are crossed out, resulting in an offspring plant that comprises one or more, but not all genes, present on the Ri plasmid.

It was found that a higher copy number of such genes results in dwarfism and other undesired properties as wrinkled leaves and decrease of flower and inflorescence number as discussed above. By the presence of only a limited number of copies of genes originating from the Ri plasmid, such disadvantages are at least partly overcome.

Preferably, the plant or progeny thereof, comprises, in the genome thereof, 1 to 5 copies of at least one or more of the rolA, rolB, rolC and rolD genes. However, also aux1, aux2 and any of the open reading frames as identified on the Ri plasmid can be included. Based on experimental data is believed that in particular rol genes play an important role in the above-described characteristics. Therefore, the disclosed plant or progeny thereof, preferably comprises, in the genome thereof, 1 to 5 copies of the rolA, rolB, rolC and rolD genes.

In a particular embodiment, the disclosed plant or progeny thereof comprises, in the genome thereof, 1 to 5 copies of the genes, present on the Ri plasmid, i.e. including the above describes rol and aux genes. Preferably the plant or progeny thereof comprises 1 to 5 copies of the Ri plasmid. However, as indicated above, it is possible to cross out one or more genes originating from the Ri plasmid in offspring of the said plant.

The number of copies is preferably 3 or less, or 2 or less or even 1. It has been found that envisaged intermediate height without concomitant adverse effects like wrinkled leaves are obtained with such a low number of gene copies.

Preferably, the plant is obtained by infection with *Agrobacterium rhizogenes* harbouring the Ri plasmid. However, it is also possible to introduce the Ri plasmid of *Agrobacterium rhizogenes* into the plant by known genetic engineering techniques, resulting in one or more genes, originating from the Ri plasmid or a combination of two or more thereof, or all four rol genes, or all genes of the Ri plasmid, being incorporated in the genome of the plant. Infection with *Agrobacterium rhizogenes* of a plant or plant cells however, has been proven very efficient and convenient. The skilled person is aware of proper techniques as how to transfect an envisaged plant with *Agrobacterium rhizogenes*.

The *Agrobacterium rhizogenes* is preferably wild-type, such as *A. rhizogenes* strain A4, deposited at the ATCC under deposit number ATCC43057, as using wild-type *Agrobacterium rhizogenes* results in transformants that are to be regarded as not being a GMO (genetically modified organism).

While any methodology can be used for producing plants, transformed with *A. rhizogenes*, in particular with one or more rol genes, the present disclosure provides both "natural" and "non-natural" methodology for generating transformed plants belonging to any of the above genera. For example, and as discussed below, applicants harnessed wild-type *A. rhizogenes* to transfer its native genes, including its rol genes into a plant cell. While this is a "natural" system in that *A. rhizogenes* transfers its native genes to plant cells, it is unlikely to successfully occur in nature because compact plants transformed with *Agrobacterium rhizogenes* face obstacles such as increased risk of fungal infection due to compact leaves forming closer structures, as well as competitiveness from neighboring plants.

The dislcosed plants or progeny thereof preferably display an intermediate height of 25-75% of a not transformed control plant, preferably of 30-70%, most preferably of 40-60%

In a preferred embodiment, the transformed plant or progeny thereof has not less than 80% of the number of flowers and/or not having a delayed flowering time by more than 4 days as compared to a not transformed control plant. It has now found by the inventor that plants, transformed with *Agrobacterium rhizogenes*, in particular rol transformed plants surprisingly have no significant loss in flower number, i.e. having at least 80%, but preferably at least 90% or 100% or even more (i.e. an increased flower number) of the number of flowers as compared to a not transformed control plant. The same is true for the delay in flowering, being preferably not later than 4 days, more preferably not later than 2 days as compared to a not transformed plant. In some transformants, flowering occurred even earlier as compared to the not transfromed control plants.

In view of the above, the disclosed plant or progeny thereof preferably belongs to any of the following genera or species:

*Kalanchoe*, in particular *K. blossfeldiana, K. laciniata, K. pinnata, K. marmorata, K. gastonis-bonnieri, K. dixoniana, K. humilis, K. ambolensis, K. aromatica, K. campanulata, K. citrina, K. coccinea, K. crundallii, K. daigremontiana, K. decumbens, K. faustii, K. fedtschenkoi, K. figueredoi, K. flammea, K. glaucescens, K. gracilipes, K. grandiflora, K. guignardii, K. jongmansii, K. laciniata, K.latisepela, K. laxiflora, K. lobata, K. longiflora, K. manginii, K. nyikae, K. obtuse, K. paniculata, K. porphyrocalyx, K. prittwitzii, K. pubescens, K. pumila, K. rauhii, K. rotundifolia, K. scapigera, K. schumacherii, K. spathulata, K. streptantha, K. synsepala, K. tomentosa, K. thyrsiflora, K. tubiflora, K. uniflora;*

*Chrysantemum*, in particular *Chrysantemum morifolium, Chrysantemum×morifolium* (syn. *C.××grandiflorum* e.g.*Dendranthema* hybrids, or hybrids between *Chrysantemum morifolium* and other *Chrysantemum* species, such as *Chrysanthemum indicum;*

*Aster*, in particular *Aster novi-belgii, Aster dumosus;*

*Rosa*, in particular *Rosa hybrida, Rosa canina, Rosa spinosissima, Rosa damascena* "trigintipetala', *Rosa centifolia;*

*Solanum*, in particular *Solanum lycopersicum, Solanum tuberosum, Solanum nicotiana;*

*Euphorbia*, in particular *Euphorbia pulcherrima, Euphorbia milli;*

*Phaelanopsis*, in particular *Phalaenopsis amabilis, Phalaenopsis amboinensis, Phalaenopsis aphrodite, Phalaenopsis appendiculata;*

*Ocimum*, in particular *Ocimum basilicum;*

*Capsicum*, in particular *Capsicum annuum, Capsicum baccatum, Capsicum chinense, Capsicum frutescens, Capsicum pubescens;*

*Mentha*, in particular *Mentha arvensis, Mentha requienii, Mentha spicata, Mentha longifolia, Mentha pulegium, Mentha suaveolens, Mentha aquatic, Mentha arvensis× spicata, Mentha aquatica×arvensis, Mentha×piperita;*

*Hibiscus*, in particular *Hibiscus rosa-sinensis, Hibiscus schizopetalus, Hibiscus sabdariffa, Hibiscus syriacus, Hibiscus trionum, Hibiscus cannabinus;*

*Mandevifia/Dipladenia*, in particular *Mandevilla×amabilis, Mandevilla sanderi, Mandevilla splendens;*

*Eustoma*, in particular *Eustoma russellianum, Eustoma exaltatum;*

*Lavendula*, in particular *Lavandula angustifolia, Lavandula latifolia,Lavandula lanata,Lavandula dentate, Lavandula stoechas, Lavandula pedunculata, Lavandula viridis;*

*Lillium*, in particular *Lilium bolanderi, Lilium×burbankii, Lilium canadense, Lilium columbianum, Lilium grayi, Lilium humboldtii, Lilium kelleyanum, Lilium kelloggii, Lilium maritimum, Lilium michauxii, Lilium michiganense, Lilium occidentale, Lilium×pardaboldtii, Lilium pardalinum, Lilium parryi, Lilium parvum, Lilium philadelphicum, Lilium pitkinense, Lilium superbum, Lilium oilmen, Lilium washingtonianum, Lilium wigginsfi;*

*Clematis*, in particular *Clematis addisonii, Clematis albicoma, Clematis alpine, Clematis aristata, Clematis* armandii, *Clematis baldwinii,Clematis bigelovii, Clematis brachiate, Clematis campaniflora, Clematis catesbyana, Clematis chinensis, Clematis chrysocoma, Clematis cirrhosa, Clematis coactilis, Clematis Columbiana, Clematis crispa, Clematis dioica, Clematis drummondii, Clematis durandii, Clematis ispahanica, Clematis fawcettii, Clematis flammula, Clematis florida, Clematis fremontii, Clematis glaucophylla, Clematis glycinoides, Clematis henryi Clematis hirsutissima, Clematis integrifolia, Clematis×jackmanii, Clematis lanuginose, Clematis lasiantha, Clematis leptophylla, Clematis ligusticifolia, Clematis macropetala, Clematis marmoraria, Clematis microphylla, Clematis montana, Clematis morefieldii, Clematis napaulensis, Clematis occidentalis, Clematis ochroleuca, Clematis orientalis, Clematis palmeri, Clematis, Clematis patens, Clematis pauciflora, Clematis pickeringii, Clematis pitcher, Clematis recta, Clematis reticulate, Clematis rhodocarpa, Clematis smilacifolia, Clematis socialis, Clematis stans, Clematis tangutica, Clematis terniflora, Clematis ternifolia, Clematis texensis, Clematis versicolor, Clematis viorna, Clematis virginiana, Clematis vitalba, Clematis viticaulis, Clematis viticella;*

*Nicotiana*, in particular *Nicotiana tabacum, Nicotiana sylvestris, Nicotiana×sanderrae;*

*Bouvardia*, in particular *Bouvardia longiflora;*

*Vanilla*, in particular *Vanilla planifolia;*

*Ipomoea*, in particular *Ipomoea batatas;*

*Echinacea*, in particular *Echinacea purpurea, Echinacea angustifolia, Echinacea pallida; Schisandra*, in particular *Schisandra chinensis, Schisandra glabra, Schisandra rubriflora;*

*Rhodiola*, in particular *Rhodiola rosea;*

*Leucanthemum*, in particular *Leucanthemum maximum, Leucanthemum paludosum, Leucanthemum×superbum, Leucanthemum vulgare, Leucanthemum adustum, Leucanthemum graminifolium, Leucanthemum integrifolium, Leucanthemum lacustre, Leucanthemum monspeliense, Leucanthemum pallens, Leucanthemum praecox, Leucanthemum subglaucum, Leucanthemum sylvaticum, Leucanthemum waldsteinii; Strelitzia*, in particular *Strelitzia reginae,* including, interspecific hybrids within the genera, and intergeneric grafts of any of the above genera and species being included as well.

In a particular embodiment, the disclosd plant belongs to any of the genera *Kalanchoe, Aster, Chrysanthemum, Clematis, Euphorbia, Hibiscus, Leucanthemum, Mandeville, Nicotiana, Ocimum, Pelagonium, Phaelanopsis, Rosa* and *Solana,* in particular suitable for ornamental use.

In another aspect, the invention relates to the use of a plant or progeny thereof as described above, as an ornamental plant, or for the provision or preparation of food, or as source for an active ingredient for the preparation of a human or animal necessity, such as a medicament, a stimulant or a cosmetic. The term 'human or animal necessity' is meant herein to mean any product, comprising any plant part, compound, mixture of compounds or extract, derived from the said plant, for use by humans or animals, in particular by treatment of said humans or animals with such a product, in particular treatment of the body thereof, such as medical, cosmetical or stimulative treatment, or consumption of the product by the said animals or humans. Food as such is therefore also to be regarded as a human or animal necessity.

In the art, only visual evaluation of plants, transformed with *A. rhizogenes* including the field crop species *Cichorum intybus* (Belgian endive) and *Nicotiana tabacum* (tabacco) as source for an active ingredient for a stimulant (cigarettes) is perfomred. The present inventor has however surprisingly found that such plants, comprising one to five *Agrobacterium rhizogenes* genes of the Ri plasmid, in particular rol genes originating from *Agrobacterium rhizogenes,* such as plants transformed with *Agrobacterium rhizogenes* or one or more rol genes thereof, or progeny thereof, not only have intermediate height, which is particularly desired when such plants grow very high, impairing harvesting, have more concentrated contents as a result of a smaller cell volume. Without being bound to any theory, is it believed that the smaller size of such transformants is at least partially due to less elongating plant cells and thus smaller cells. This is pronounced in that e.g. the fruits of rol transformed fruits such as peppers from Capsicum species, or vanilla from *Vanilla planifolia,* or herbs, such as basil (*Ocimum basilicum*) have an intensified taste as compared to non-transformed counterparts. The same is true for tomato, potato and monocots such as wheat, barley etc. The same is true for plants used as source for an active ingredient for the preparation of a medicament or a stimulant. Such plants, such as medicinal plants, have the active ingredient in a more concentrated fashion in their cells, therewith facilitating isolation and extraction thereof. In case of tobacco, comprising the stimulant nicotine, has a higher nicotine content, resulting in a more concentrated product. More details of use of plants, plant parts, compounds, and mixtures of compounds or extracts for use as human necessities are given in the examples.

Plants for use for the provision or preparation of food preferably belong to any of the genera *Vanilla, Ocimum, Capsicum, Ipomoea, Solanum,* although any such plant is encompassed by the invention. The plant itself can be used as food, such as carrots, or fruits thereof, such as apples, pears, berries, etc. also, extracts can be prepared, such as e.g. tea.

The plant for use as source for an active ingredient for the preparation of a medicament or stimulant preferably belongs to any of the genera *Kalanchoe, Solanum, Nicotiana, Rhodiola, Echinacea, Schisandra, Rosa, Hibiscus* and *Chrysanthemum.* rol transformed *Kalanchoe* comprises elevated levels of bryophillins, such as bryophillin A, having a strong anti tumor promoting activity, and interestingly, the levels of the flavonoids kaempferol and isohamnetin increased significantly in plants as decribed herein, in particular in Kalanchoe, rendering extracts of such plants of particular interest in cancer treatment. rol transformed *Schisandra* contains elevated levels of schisandrin, desoxyschisandrin, gomisins and pregomisin. *Echinacea,* rol transformed, has elevated levels of e.g. propanoid and echinacoside.

Therefore, the invention also relates to an extract of a plant or progeny thereof as described herein for use as a medicament, in particular Kalanchoe extract for use as a medicament for treatment of cancer, or any other disease or condition, that can be alleviated by the action of antioxidants, in particular flavonoids, such as oxygen radical induced diseases.

Also, extract of leaves of rol transformed *Chrystantenum morfolium* or *Hibiscus sabdariffa* can be used for the preparation of tea, *Rosa* spp can be used for the preparation of perfumes etc.

In another aspect, the invention relates to a method for the preparation of a plant as described above, comprising the steps of:

(a) transforming tissue of the wild type plant with the Ri plasmid of *Agrobacterium rhizogenes,*

(b) allowing the transformed tissue to develop roots having a hairy phenotype,
(c) selecting, among the roots with hairy phenotype of step (b), a root where the hairy phenotype shows a maximum root hair length of at most half of the maximum root hair length observed in the roots obtained in step (b);
(d) growing the selected root on a regeneration medium and allowing a transformed rooted plantlet to generate from the said selected root;
(e) growing said transformed rooted plantlet into a mature transformed mother plant having a height of 25-75% of that of the corresponding wild type plant.

It has surprisingly found that plants transformed with one to five genes originating from the Ri plasmid of *Agrobacterium rhizogenes*, can be obtained this way without having the above disadvantages or to a significant lesser extent. Herein, the phrases 'genes originating from *Agrobacterium rhizogenes*', or 'Ri genes' are as defined above and are particularly intended to mean 'genes originating from the Ri plasmid of *Agrobacterium rhizogenes*', in particular from the $T_L$- and $T_R$-DNA of the Ri plasmid as shown in SEQ ID NOs 1 and 2, respectively.

In step (a), tissue, such as leaf discs of the wild type plant are transformed with the Ri plasmid of *Agrobacterium rhizogenes*, resulting in incorporation of one or more of the genes originating from the Ri plasmid in the genome of the transfected plant cells. As indicated above, the skilled person is aware about how to introduce the Ri plasmid in the plant in such a way that it results in expression in the transformed plant cells of one or more of the genes originating from the Ri plasmid. The plant can e.g. be obtained by infection with *Agrobacterium rhizogenes*, e.g. by contacting a culture of *Agrobacterium rhizogenes* with a fresh wound of the plant or a portion thereof. However, it is also possible to introduce, by known genetic engineering techniques, the Ri plasmid into plant cells, resulting in expression of a gene originating from the Ri plasmid or a combination of two or more thereof, such as one or more rol genes, a combination of two or more thereof, or all four rol genes, by the plant cells. Infection with *Agrobacterium rhizogenes* of a plant or plant cells however, has been proven very efficient and convenient. The skilled person is aware of proper techniques as how to transfect an envisaged plant with *Agrobacterium rhizogenes*, and how the produce transformed plants.

In a subsequent step, the thus transformed tissue is allowed to develop roots, followed by a specific way of selecting one or more roots with hairy root phenotype, a well-known phenotypic selection marker for *A. rhizogenes* transformed plant tissue. However, in contrast to the art, wherein selection is made for the most hairy transformants having the most and the longest hairs on the roots, the present inventors surprisingly found that by selecting for less hairy roots as defined in step (c), preferentially plants with intermediate height are obtained instead of plants showing dwarf growth. It was surprisingly found that the less hairy roots as selected according to this embodiment of the invention are produced by plants having less copies of the genes originating from the Ri plasmid. In a normal transformation event, transformants contain over more than 10 copies of the genes originating from the Ri plasmid. By selecting tissue portions having hairy roots of which the hair length is at most half of those having the maximum length, the envisaged transformants are found. Those having maximum hair length comprise over 10 copies of the Ri genes.

After the selection, the selected less hairy roots are grown on a regeneration medium, so that transformed rooted plantlets can be generated therefrom, which can subsequently be grown to maturity. Such a mature transformed mother plant comprises 1 to 5 copies of the gene(s) originating from the Ri plasmid and will have the envisaged intermediate height of 25-75% of that of the corresponding wild type plant, such as a control plant of the same species, as descried above, that can be generated by performing the same steps of the described method, and from the same tissue material however without being subjected to the transforming step. However, another wild type plant of the same species can also be use as and indication for the normal wild type plant height.

In an attractive embodiment, the selection step (c) also comprises selecting, among the roots with hairy phenotype of step (b), a root where the hairy phenotype shows a number of branches per length that is at most half of the maximum number of branches per such length observed in the roots obtained in step (b). In addition to the root hair length, branching is also a selection criterion for transformants that contain only 1 to 5 copies of Ri genes, which selection criterion can be used together with the above criterion of hair length, or instead thereof. Preferably both criterions are taken into consideration. If the number of branches per length of the hairy roots is half of that of those transformants with the mostly branched roots, such transformants contain the envisaged lower copy number of Ri genes.

While selecting, it is advantageous to check the root development on control plants, that are grown from untransformed tissue portions.

Based on the knowledge, the inventor gained by the above method, another method could be developed, without the specific selection step, but by 'diluting' the Ri genes out of the genome of the transformants by crossing and backcrossing of the obtained transformed mother plants. In that case, the transformed mother plants do have more than 10 copies of the Ri genes after transformation, and often show dwarf growth and other disadvantages as described above. By selecting offspring of the transformed mother plant until the envisaged intermediate height is obtained, plants having 1 to 5 copies of the Ri gene(s) in their geneome. To this end a second method for the preparation of a plant as described above is provided, comprising the steps of:
  (a) transforming tissue of the wild type plant with the Ri plasmid of *Agrobacterium* rhizogenes,
  (b) allowing the transformed tissue to develop roots having a hairy phenotype,
  (c) selecting a putatively transformed root having a hairy root phenotype;
  (d) growing the selected root on a regeneration medium and allowing a transformed rooted plantlet to generate from the said selected root;
  (e) growing said transformed rooted plantlet into a mature transformed mother plant;
  (f) generating progeny of the mature transformed mother plant of step (e) by crossing, backcrossing and selfing, while selecting for progeny having an increased height as compared to the mature transformed mother plant of step (e) and a reduced height as compared to that of the wild type plant of step (a),
  (g) repeating step (f) until the progeny results in mature plants having a height of 25-75% of that of the corresponding wild type plant of step (a).

In this embodiment, step (c) merely selects for the presence of hairy roots, without the need to investigate the hair length or number of branches in more detail. Instead, additional step (f) is added, wherein the mature transformed mother plant of step (e), which will presumably show dwarf growth habits (i.e. having a length of less than 20% of the corresponding wild type plant) is subjected to one or more crossing or backcrossing or selfing steps, that results in offspring of the envisaged intermediate height. By such further crossing, additional functions can be introduced, or present functions can be further improved or removed from the plant in later generations. The hybrids of the progeny can be further crossed and selected, and this can be repeated several rounds in order to arrive at the envisaged result.

Preferably, in the above described method, step (e) or, if present, step (f) and/or (g) comprises selecting for a plant height of 30-70%, preferably 40-60% of of that of the corresponding wild type plant. If in the second method plants of the envisaged height are already obtained during step (e), a selection for those plants may even make steps (f) and (g) of less importance or superfluous. The same is true when in step (f) plants of the envisaged height ar obtained. In that case, step (g) is superfluous.

Preferably, step (e) or, if present, step (f) and/or (g) further comprises selecting for plants or progeny, having not less than 80%, preferably not less than 90% of the number of flowers and/or not having a delayed flowering time by more than 4 days, preferably by more than 2 days, as compared to a not transformed control plant. It has been found that such plants are generated when it comprises 1 to 5 copies of one or more of the genes originating from the Ri plasmid, and can be selected for.

In an attractive embodiment, step (a) comprises co-cultivating A. rhizogenes harbouring the Ri plasmid with a plant or plant part, such as a leaf or leaf portion, allowing A. rhizogenes to deliver the Ri plasmid into said plant or plant portion. As indicated above, the Ri plasmid can be introduced in the plant cells by any known transformation technique, it is preferred to co-cultivate A. rhizogenes with a plant or plant portion, e.g. including wounding the plant or plant part.

In the described methods, by co-cultivating A. rhizogenes with a plant or plant part, one or more genes originating from the Ri plasmid of Agrobacterium rhizogenes are incorporated in the genome of plant cells, and preferably comprise one or more rol genes, in particular chosen from rolA, rolB, rolC and rolD, as described above. In particular, also aux1, aux2 and any of the open reading frames as identified on the Ri plasmid are included, e.g. as a result of complete integration of the Ri plasmid in the plant genome.

In a preferred embodiment, step (a) comprises infection with Agrobacterium rhizogenes, which is a natural way of transformation without the need of applying genetic manipulation techniques. While any methodology can be used for transforming plants with the Ri plasmid of A. rhizogenes, the present disclosure provides both "natural" and "non-natural" methodology for generating transformed plants, in particular belonging to any of the genera as described above. For example, and as discussed below, applicants harnessed wild-type A. rhizogenes to transfer its native genes, including its rol genes into a plant cell. While this is a "natural" system in that A. rhizogenes transfers its native genes to plant cells without the presence of foreign DNA (i.e. not belonging to the DNA of A. rhizogenes or the host cell), it is unlikely to successfully occur in nature because compact plants transformed with Agrobacterium rhizogenes face obstacles such as increased risk of fungal infection due to compact leaves forming closer structures, as well as competitiveness from neighboring plants. Apart therefrom, as transformed plants will in nature contain many copies of the Ri plasmid, this results not only in dwarf growth, but also in delayed flowering, making crosspollination with wildtype plants impossible.

The Agrobacterium rhizogenes is preferably wild-type, such as strain A4 (ATCC43057), i.e. not containing genetic material that has been introduced by way of genetic engineering. Advantageously, using wild-type Agrobacterium rhizogenes results in transformants that are to be regarded as not being a GMO (genetically modified organism).

Preferably, the above methods comprise assaying the number of copies of one or more genes originating from the Ri plasmid of Agrobacterium rhizogenes, enabling to select for plants with a reduced number of copies of the Ri plasmid or one or more genes thereof. Preferably, after such assay, a selection is made for plants having 1 to 5 copies of the Ri plasmid or one or more genes thereof. A possible assay is explained in the examples below, but the skilled person in the art of molecular biology will be aware of any suitable and applicable assays.

In a very attractive aspect, the invention relates to a product, comprising a plant part, extract, compound or a mixture of two or more thereof, derived from a plant as described herein or progeny thereof. Said product can e,g, be chosen from the group, consisting of fruits, tubers, roots, leaves, food extracts, cosmetics, medicaments, perfumes. But such product is not limited thereto. For example, fruits such as peppers or tomatoes, or tubers such as potatoes have a more intense taste as from plants, not being transformed with Agrobacterium rhizogenes, such as non rol transformed plants. Said products can be identified by the presence of genetic material encoding rol genes or parts thereof. Said presence can conveniently be identified e.g. by PCR techniques, e.g. as exemplified herein.

The following figures and examples are illustrative and do not limit the present application. Of course, it is understood that many variations and modifications can be made while remaining within the intended spirit and scope.

FIG. 1 depicts an illustrative A. rhizogenes Ri-plasmid from an agropine strain. The T-DNA contains two segments, $T_L$ and $T_R$, which are separated by a 15 Kb sequence that is not integrated. The $T_L$-DNA contains 18 open reading frames (ORFs) where the four root loci-genes reside. The $T_R$-DNA contains several genes, including aux1 and aux2.

FIGS. 2, 3 and 4 show roots of leaf discs of Solanum tuberosum, Dipladenia and Kalanchoe interspecific hybrid 2006-0199 (K. laciniata×K. blossfeldiana hybrid) respectively that have been exposed to Agrobacterium rhizogenes. A: non transformed control, B: transformed, hairy, C: transformed, less hairy.

FIG. 5A shows a Kalanchoe interspecific hybrid 2006-0199 wild type (left) and Kalanchoe interspecific hybrid 4006-0199S2, regenerated from less hairy roots of (FIG. 4C), transformed with Agrobacterium rhizogenes, fifteen weeks after start of vegetative propagation under long day conditions (light from 02:00 to 17:00). Three weeks after sticking the cuttings the plants were moved to short day conditions for flower induction (light from 07:00 to 17:00). FIG. 5B shows a Kalanchoe interspecific hybrid 2006-0199 wild type (left) and and Kalanchoe interspecific hybrid 4006-0199K20.1 transformed with Agrobacterium rhizogenes (3 plants to the right) of the hairy type, regenerated from roots of FIG. 4B, fifteen weeks after start of vegetative propagation under long day conditions (light from 02:00 to 17:00). Three weeks after sticking the cuttings the plants were moved to short day conditions for flower induction (light from 07:00 to 17:00).

EXAMPLES

Plant Material

In vivo plants of Kalanchoe pinnata, Kalanchoe interspecific hybrid 2006-0199, (Knud Jepsen A/S, Hinnerup, Denmark and AgroTech a/s, Tåstrup, Denmark) were cultivated in a greenhouse with temperatures of 20° C. at day and night, 16 hour day length and a light intensity of 260 µmol photons $m^{3 1 \, 2} \, s^{-1}$. In vitro plants were cultivated in growth chamber with temperatures of 25° C. at day and 22° C. at night, 13 hour day length and a light intensity of 75 µmol photons $m^{-2} s^{-1}$. Plants of other species were purched from different suppliers.

Leaf explants for each species/hybrid were used for control experiment. Leaves derived from in vivo material were sterilised in 70% EtOH for 1 min. followed by 20 min. in 1% NaOCl (VWR, Copenhagen, Denmark) and 0,03% (v/v) Tween 20 (Merck, La Jolla, USA) and washed 3 times in sterile water and were stored until excision.

Bacterial Strain

Agrobacterium rhizogenes strain ATCC43057 (A4) (kindly provided by Dr. Margareta Welander, Swedish University of Agricultural Sciences, Sweden) was used for induction of hairy roots. The strain was cultured in liquid MYA medium (Tepfer and Cassedelbart (1987) Microbiol Sci. 4, pp. 24-28. 1 mL of the bacterial glycerol stock (kept at −80° C.) was diluted in 10 mL MYA in a 50 mL Falcon tube and incubated for 8 h at 27° C. and shaken at 260 rpm. The solution was further diluted with 100 mL MYA in a 250 mL flask and shaken at 260 rpm for 24 h in darkness at 27° C. The $OD_{600}$=0,4-0,6 was measured on Nanodrop 1000 (Thermo Scientific, Wilmington, Del., USA).

Transformation

Figure 1:
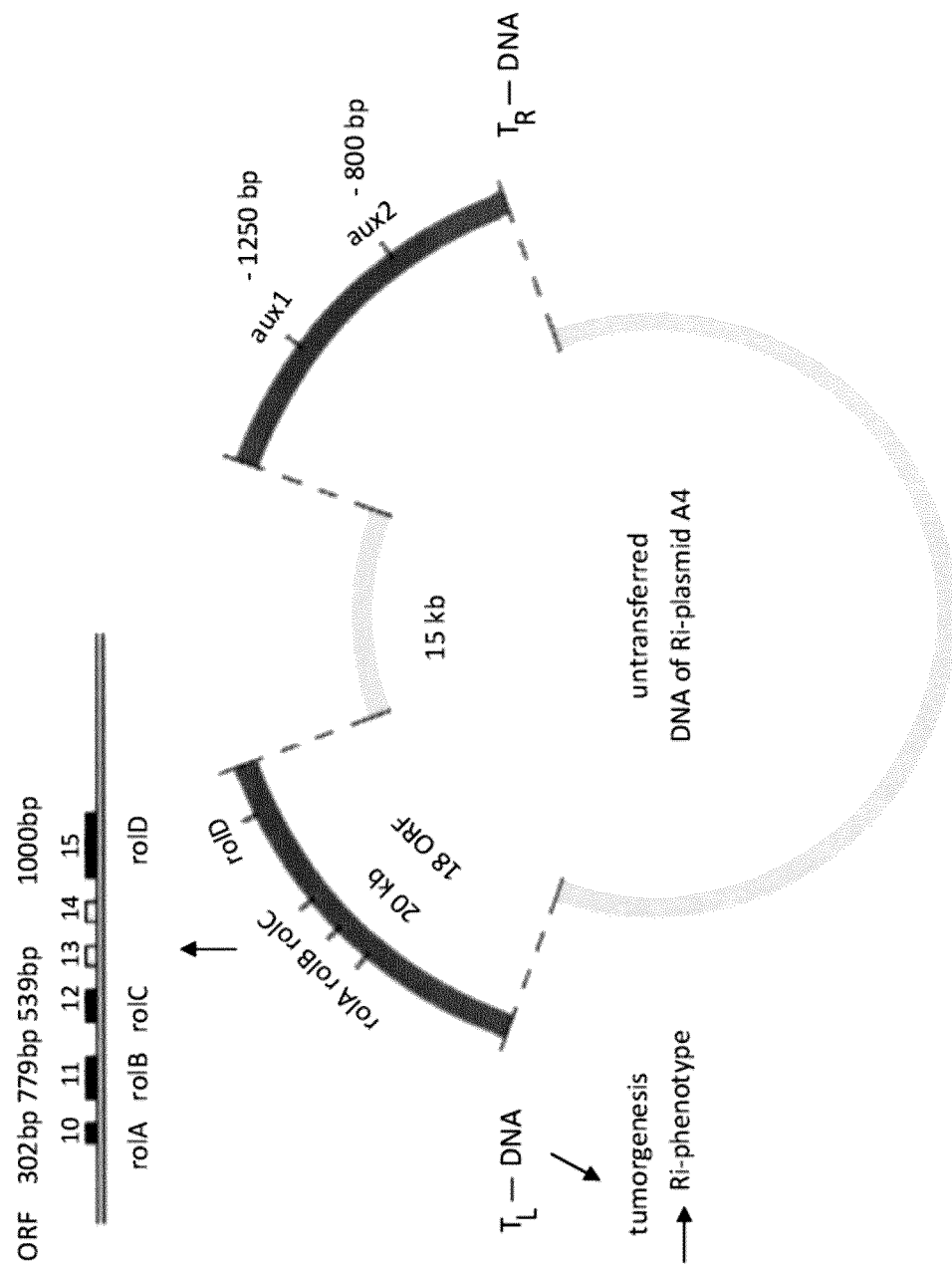
Figure 2A:
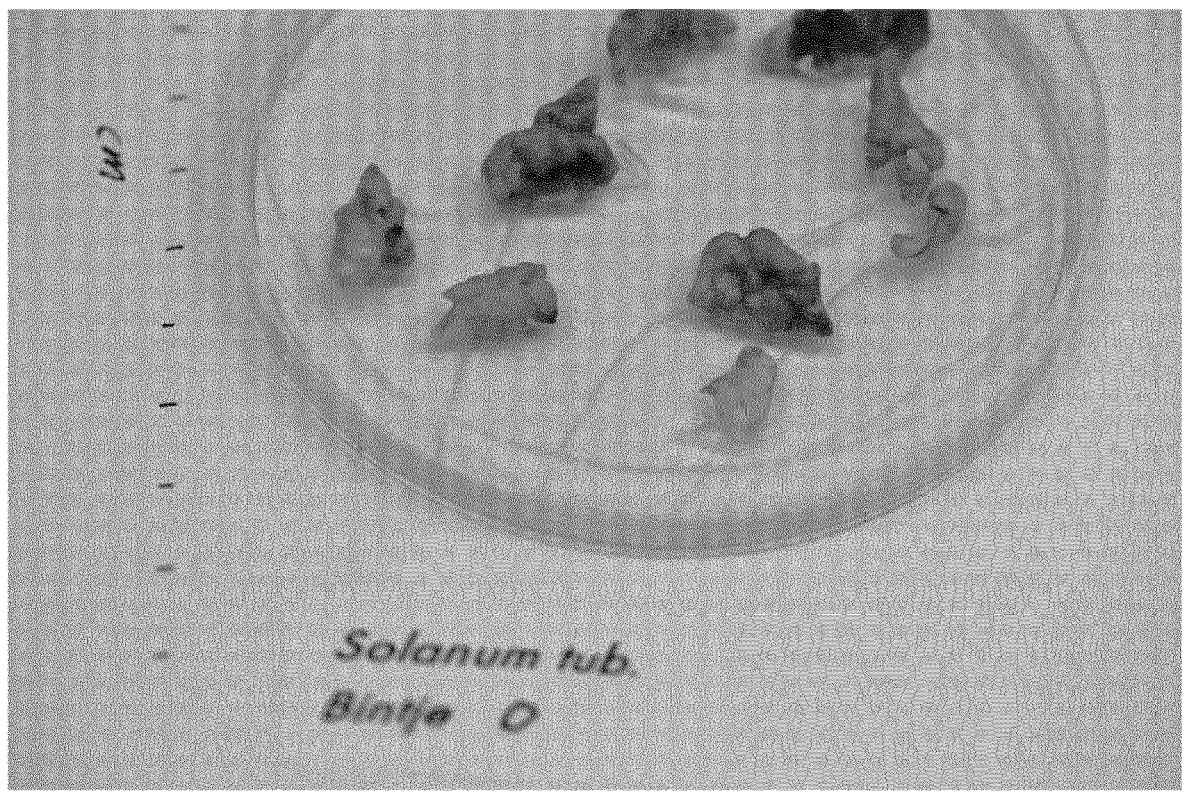
Figure 2B:
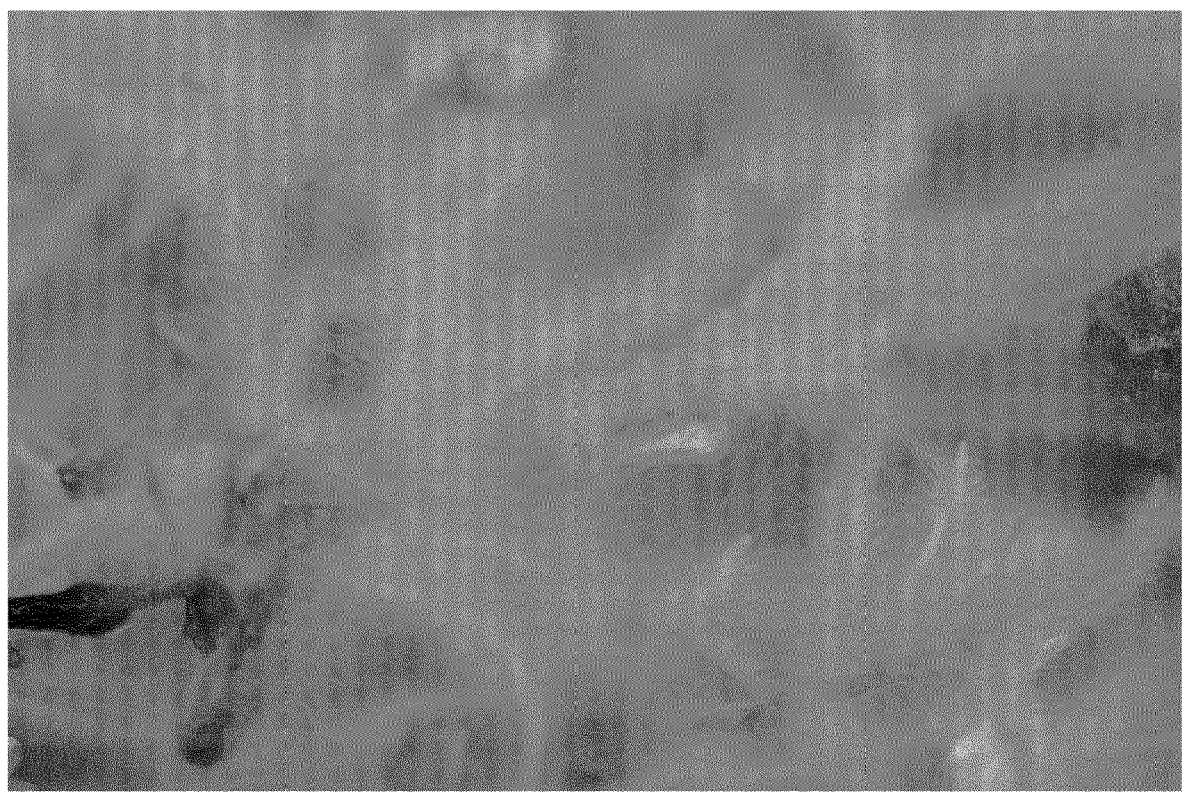
Figure 2C:
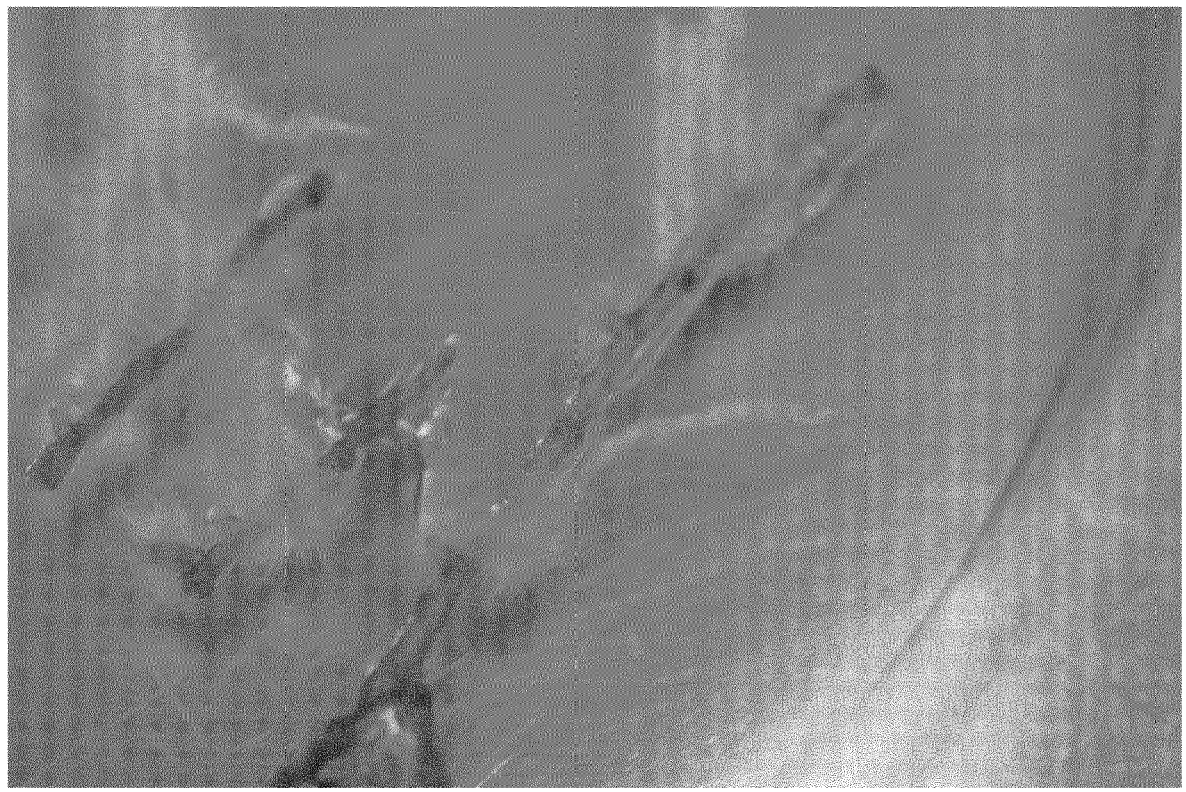
Figure 3A:
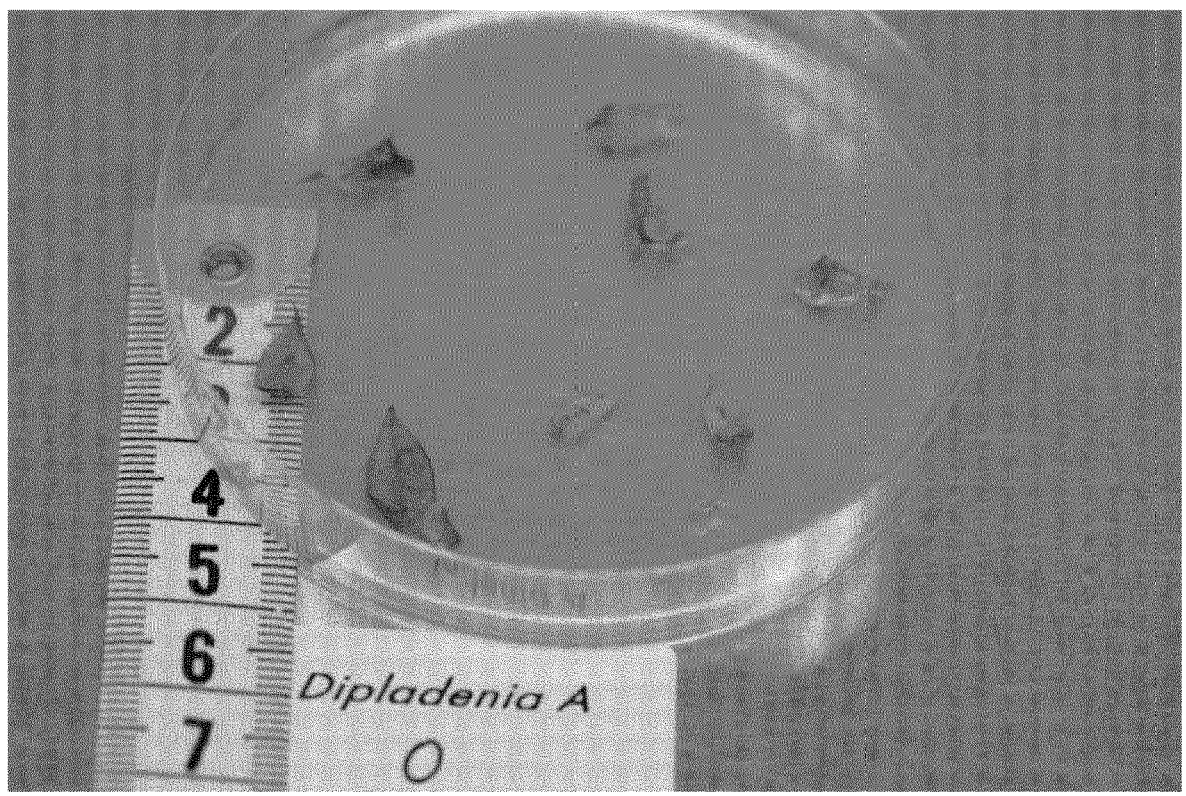
Figure 3B:
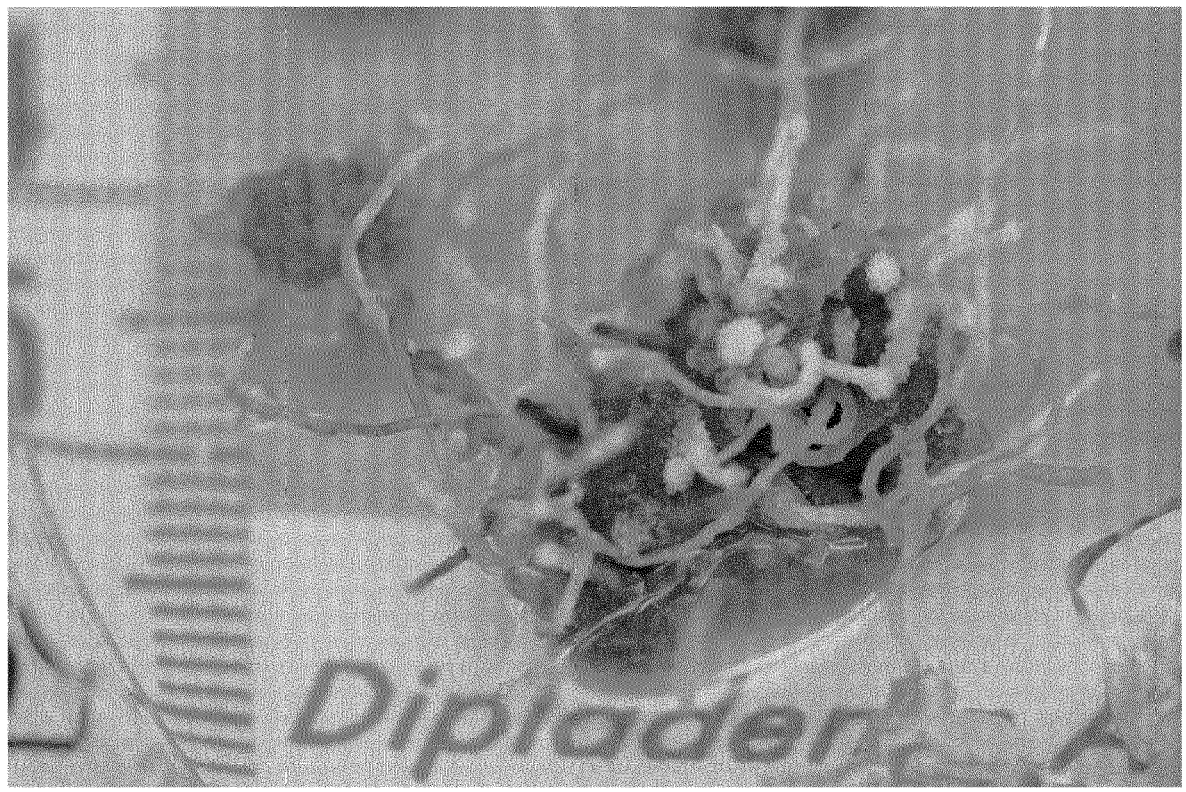
Figure 3C:
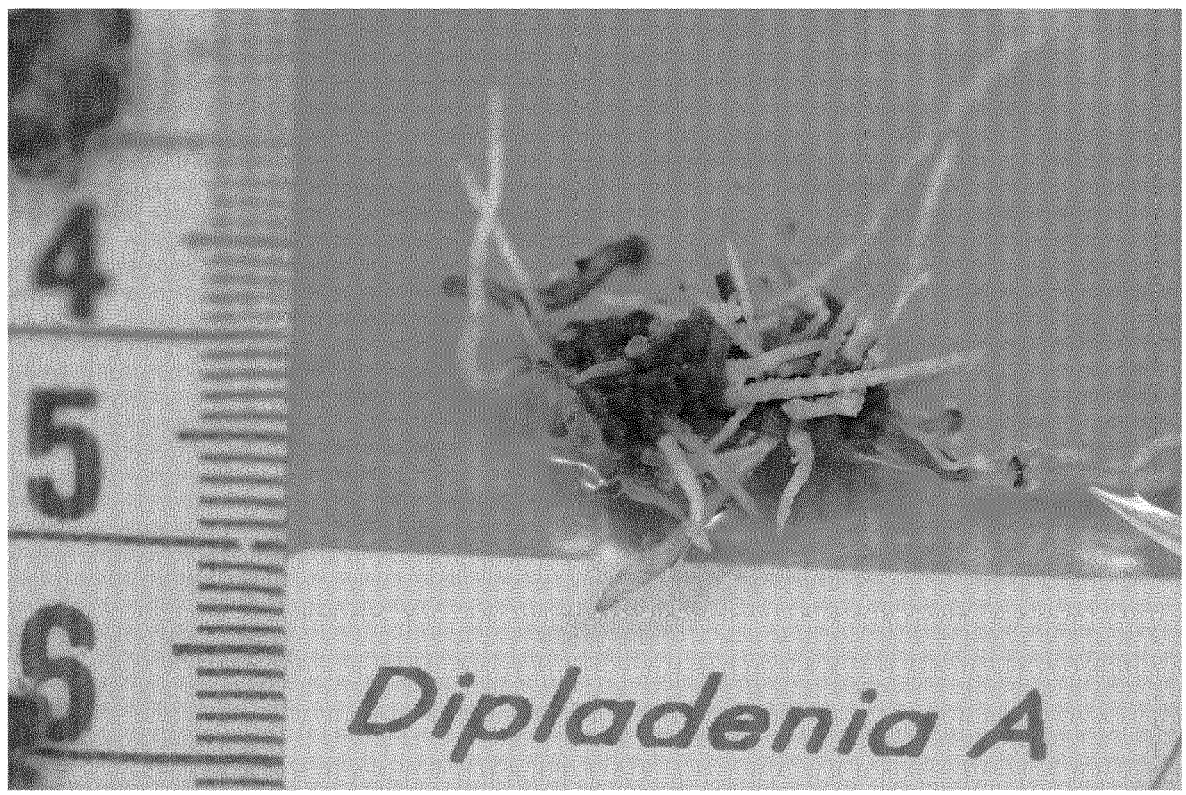
Figure 4A:
Figure 4B:
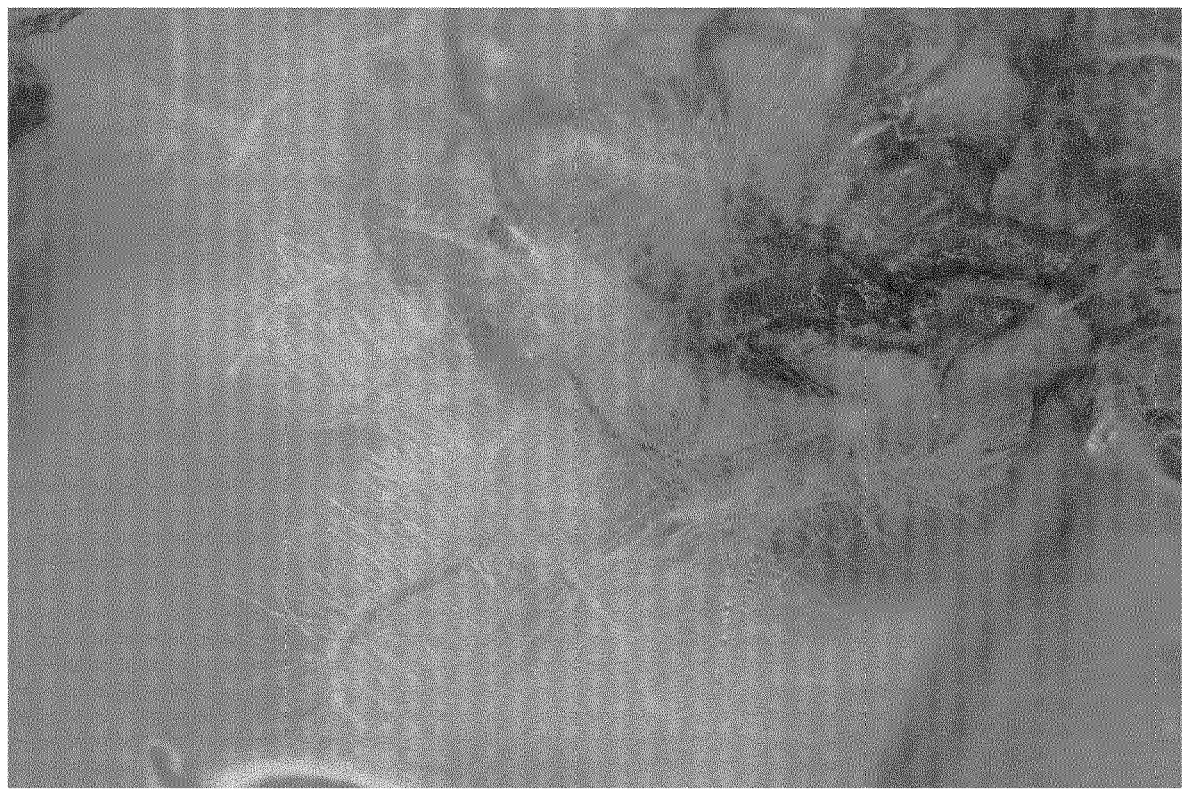
Figure 4C:
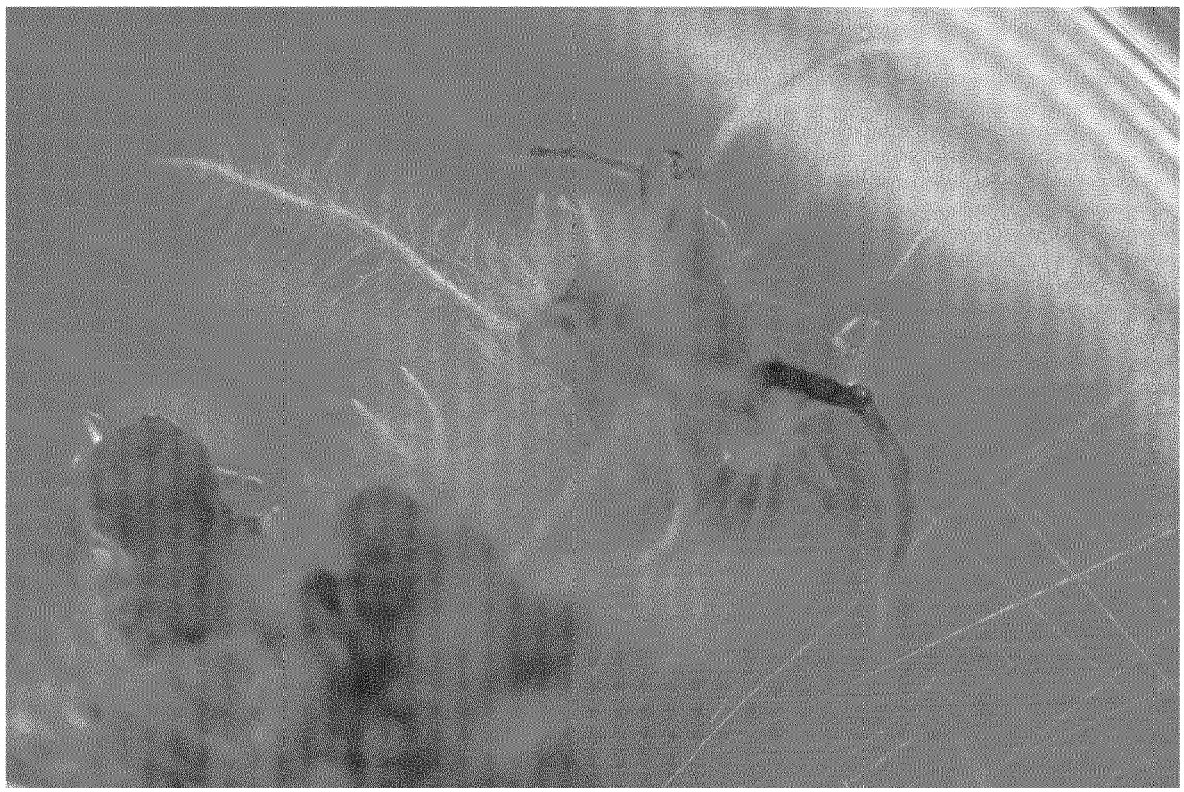
Figure 5A:
Figure 5B:
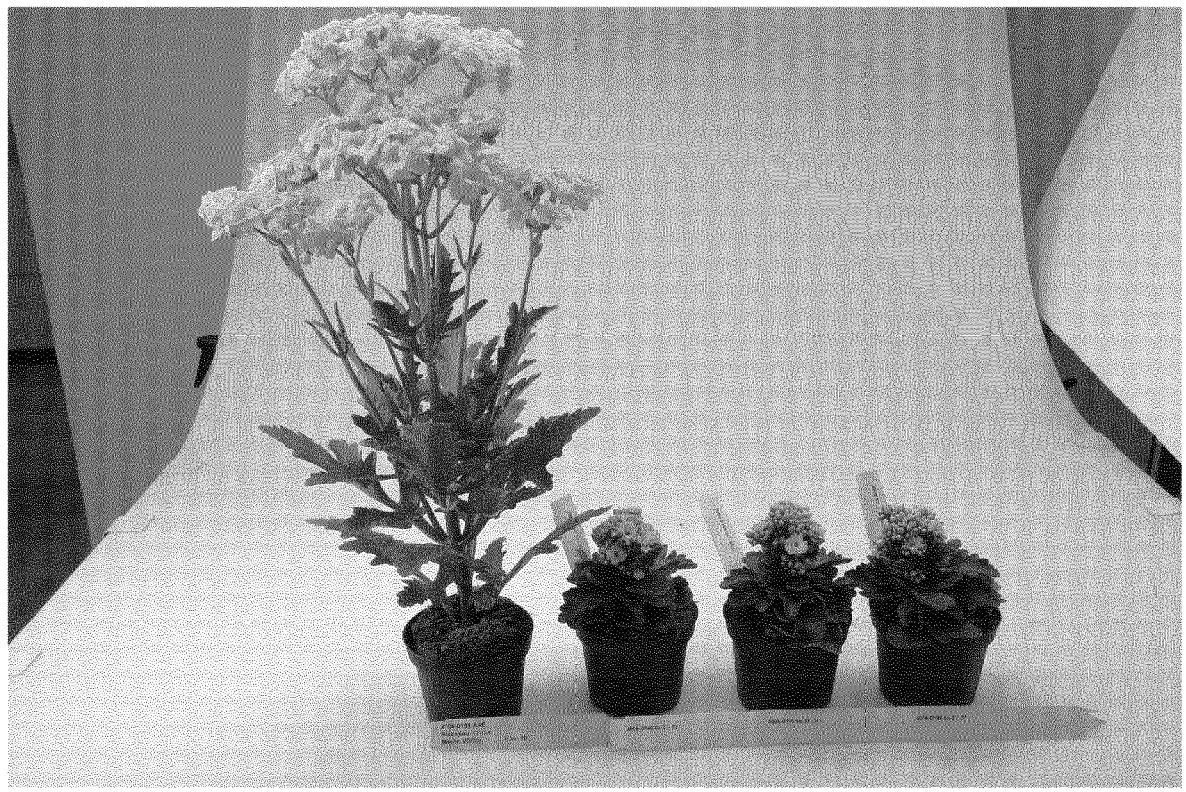
Figure 6:
FIG. 6 shows Kalanchoe pinnata AAE, rol transformed (left) and a control wild type plant (right), The plant of intermediate height (middle, K.pinnata rol-2 Pemba) was obtained by crossing and back crossing of a rol transformed plant of the left.
Figure 7:
FIG. 7 shows Rosa, rol transformed (left and middle) and a control wild type plant (right). The plant with intermediate height (middle) originates from a selection for less hairy roots.
Figure 8:
FIG. 8 shows Aster, rol transformed (left and middle) and a control wild type plant (right). The plant with intermediate height (middle) originates from a selection for less hairy roots.

Sterilized leaves or in vitro plant were excised to pieces of min 1 cm×1 cm and stored in sterile water until all explants were ready. The water was discarded from the explants and A. rhizogenes-suspension was added to cover all explants for 30 min. After 30 min. the A. rhizogenes-suspension was discarded and the slices were transferred, with a thin layer of the A. rhizogenes suspension on the surface, to co-cultivation plates for 24 h in darkness without selection. The explants were cultivated in the lab at temperatures at 22° C. in darkness. After co-cultivation the explants were transferred to 0-media (selection media) by drying the explants with pieces of ripped sterile filter paper. The leaf surface was as dry as possible on both sides of the excised leaf. The explants stayed in darkness until roots were developed enough to be transferred to regeneration media. The material was transformed over three sessions. The transformation was conducted with Solanum tuberosum (see FIG. 2), Dipladenia (see FIG. 3), Kalanchoe interspecific hybrid 2006-0199 (K. laciniata×K. blossfeldiana hybrid) (see FIG. 4-5), Kalanchoe pinnata (see FIG. 6), Rosa hybrida (see FIG. 7) and Aster novo-belgii (see FIG. 8). For each species the controls and putative transformants was performed the same day.

Basic Medium

The basic medium used as background of all media used was ½× MS (Sigma M0404) (consisting of Murashige and Skoog macro- and microelements) (Murashige and Skoog, 1962) at a concentration of 2,2 g $L^{-1}$, 30 g $L^{-1}$ sucrose (table sugar), 7 g $L^{-1}$ bacto agar and 0,50 g $L^{-1}$ 2-(N-morpholino)-ethanesulphonic acid (MES) (Duchefa). The pH was adjusted to 6.3 by 1 M KOH and the media was autoclaved at 121° C. and 103,5 kPa.

Co-Cultivation Medium

Co-cultivation medium used for co-cultivation between explant and A. rhizogenes consisted of basic medium with 30 µg $mL^{-1}$ acetosyringone (Sigma-Aldrich, Steinheim, Germany).

Selection Medium

Selection medium was a hormone-free medium used for root formation of putatively transformed explants and controls. Filter-sterilized antibiotics were added after autoclaving to the selection media to the basic medium. Selection media consist of basic media ½× MS medium with timentin (TIM) in the concentration of 100 mg $L^{-1}$. Preferably, the selection medium contains arginine, preferably 0.5 mM arginine.

Regeneration Media

Regeneration medium containing the hormone N-(2-chloro-4-pyridyl)-N-phenylurea (CPPU) was used for regeneration of nodules on the putatively transformed root clusters. Filter-sterilised hormones and antibiotics were added after autoclaving to the regeneration media. The CPPU-medium contained basic ½× MS medium with 1.5 µg $L^{-1}$ CPPU together with TIM in the concentration 100 mg $L^{-1}$.

Co-Cultivation

In all treatments the explants were co-cultivated for 24 hours. After co-cultivation, the explants were blotted onto sterile filter paper and thoroughly dried with ripped pieces of sterilised filter paper. Controls and putatively transformed explants were transferred to selection medium.

Plant Selection

After 24 hours of co-cultivation the explants were transferred to 0-media (selection medium) with 8 explants on each Petri dish. After several weeks the increasing number of roots and decreasing number of explants (due to vitrification—the leaf sections became glass like or because of infections) were monitored for the specific Petri dish in the treatment.

Plant Regeneration

When the roots of putatively transformed explants had developed to a length of 1.5-2 cm they were transferred in clusters, with a part of the explant to CPPU-medium. The transferred root clusters were placed in a climate chamber (Celltherm, United Kingdom) on shelves with 11 h daylight and day/night temperatures of 20/18° C. and an intensity of 45-70 µmol photons $m^{-2}s^{-1}$ (Philips, Amsterdam, The Netherlands). Only root clusters with A. rhizogenes treated explants was transferred. Here the number of root clusters was monitored as well as the number of nodules developing from the roots. Counting of nodule development was stopped when no positive development was observed after 30 days for any of the four species.

Control Plants

Control plants were treated like transformants but inoculated in MYA medium without bacteria and with a lower number of explants-25 per cultivar. The control experiment plants were conducted in parallel with the transformants.

Plant Growth Conditions

Plants described herein were grown in a greenhouse according to day length and temperatures as described in tables 1 and 2 below. The plants were produced in pots with a diameter of 10.5 cm or 13 cm. Cuttings were taken from vegetative (veg.) plants and grown and kept vegetative for the first 3-8 weeks following planting, depending on cultivar, species, genus and pot size. The plants described in table 1 were transferred to flower inducing conditions 4-9 weeks after planting. Between 13-19 weeks after planting, depending on cultivar, species genus, pot size, and time of year, the plants entered their generative (gen.) stage—were mature with flowers that were opening or about to open.

The plants were grown under natural light conditions supplemented with 70 µmol photons $m^{-2}s^{-1}$ SON-T light when the natural light was less than 100 µmol/$m^2$/s. All plants, except *Phaelanopsis* and *Vanilla*, were grown in a peat based soil mix and were watered with a solution containing 200 parts per million (ppm) nitrogen, 200 ppm potassium, 40 ppm phosphorous, 200 ppm calcium, 40 ppm magnesium, 60 ppm sulphate, 1 ppm iron, 0.6 ppm manganese, 0.1 ppm copper, 0.1 ppm zinc, 0.3 ppm borium, 0.03 ppm molybdenum. For all plants, except *Phaelanopsis* and *Vanilla*, shading with curtains was active when light intensity was higher than 450 µmol photons $m^{-2}$ $s^{-1}$ and humidity was kept in the range between 60-80% relative humidity.

*Phaelanopsis* and *Vanilla* were grown in a bark based soil mix and were watered with a solution containing 50 parts per million (ppm) nitrogen, 50 ppm potassium, 10 ppm phosphorous, 50 ppm calcium, 10 ppm magnesium, 15 ppm sulphate, 0.2 ppm iron, 0.1 ppm manganese, 0.01 ppm copper, 0.01 ppm zinc, 0.05 ppm borium, 0.005 ppm molybdenum.

*Vanilla* and *Phaelanopsis* plants were grown under natural light conditions. Shading with curtains was active when light intensity was higher than 250 µmol photons $m^{-2}$ $s^{-1}$ and humidity was keep in the range between 80-90% relative humidity.

Molecular Analysis

Six independent DNA isolations per sample have been done with Nucleomag 96 plant, (http:/www.mn-netcom/) on a KingFisher Flex (thermo scientific) according suppliers recommendations, with the modification that lysis buffer MC1 of the Nucleomag 96 plant kit has been supplemented with 1% PVP.

qPCR Amplification was done in a DNA thermal cycler (CFX96 Touch Real-Time PCR Detection System, Bio-Rad) according to the following program: 92° C. for 2 min, followed by 45 cycles of 92° C., for 20 s, 59° C. for 20 s, and 72° C. for 20 s. The reactions for rolC and Ref1, table 1, where individually labelled with LCgreen+by using SALSA Polymerase according to the supplier's instructions (BioFire Defense, http://biofiredefense.com/; MRC-Holland, www.mlpa.com).

TABLE 3

Primers used

| primer # | target | sequence | |
|---|---|---|---|
| 2142 | rolC F | CAATAGAGGGCTCAGGCAAG | SEQ ID NO 9 |
| 2143 | rolC R | CCTCACCAACTCACCAGGTT | SEQ ID NO 10 |
| 1654 | Ref1 | AATGAGGGCTTGTTGGATGA | SEQ ID NO 11 |
| 1655 | Ref1 | TTTGAGTGATGGCTCCTTCC | SEQ ID NO 12 |

The use of $\Delta C_t$ assumes that the two reactions have similar efficiencies and that they proceed in an independent way since they were carried out in separate wells. A relative quantification has been done by $$\Delta C_t = C_{t(rolC)} - C_{t(Ref1)}$$

and ratio was calculated by $$2^{-\Delta Ct}$$

TABLE 1

Growth conditions

| | Light period (Max Light) | Dark period | Light temp | Night temp. | Genus |
|---|---|---|---|---|---|
| Short day | 07:00-17:00 | 17:00-07:00 | 19° C. | 21° C. | *Kalanchoe* (gen.), *Aster* (gen.), *Chrysanthemum* (gen.), *Euphorbia* (gen.), *Bouvardia* (gen.), *Rhodiola* (veg.) |
| Long day | 02:00-17:00 | 17:00-02:00 | 19° C. | 21° C. | *Kalanchoe* (veg.), *Aster* (veg.), *Chrysanthemum* (veg.), *Euphorbia* (veg.), *Bouvardia* (veg.), *Rhodiola* (gen.), *Strelitzia*, *Hibiscus*, *Mandevilla*, *Echinacea*; *Schisandra*, *Rosa*, *Ocimum*, *Capsicum*, *Ipomoea*, *Solanum*, *Nicotiana* |

TABLE 2

Growth conditions for *Vanilla* and *Phaelanopsis* plants

| | Light period | Dark period | Light temp | Night temp. |
|---|---|---|---|---|
| Vegetative growth before flowering | 06:00-18:00 | 18:00-06:00 | 24° C. | 24° C. |
| Cooling for flower induction | 06:00-18:00 | 18:00-06:00 | 14-17° C. | 14-17° C. |
| Generative growth after flower induction | 06:00-18:00 | 18:00-06:00 | 24° C. | 24° C. | and the copy number is calculated on the basis that the analysed plants where primary transformants of tetraploid plants and therefor the ratio is multiplied by 4 in order to get the copy number.

In order to determine the copy number of a primary tetraploid transformant a qPCR on rolC of *A. rhizogenes* with Ref1 as an internal Kalanchoe reference has been done on an untransformed control plant 2006-0199 (an interspecific hybrid having *K.laciniata* and *K.blossfeldiana* as parental lines), 3 independent primary transformants of said control plant (i.e. obtained by selection of the transformants without further crossing based on root morphology as described herein), 4006-0199K20.1, 4006-0119S11 and 4006-0199S2, as well as on Ri line 331 as described by Christensen, 2008, supra. Said transformants differ in their growth habit, table 1. For 2006-0199 as expected no rolC could be detected and hence on ratio or copy number could be determined, in case of the 3 *A. rhizogenes* transformants there is a clear difference in copy number compared to the reference gene Ref1. The semi-compact transformants 4006-0199S11 and 4006-0199S2 having intermediate height, have one copy of rolC compared to Ref1, whereas the compact transformant 4006-0199K20.1 showing dwarf growth has 11 copies of rolC, whereas Ri line 331 showed intermediate height, see table 4. It was also observed that the transformants 4006-0199S11 and 4006-0199S2 showed a similar flower number as the control, and no leaf wrinkling, whereas both 4006-0199K20.1 and Ri line 331 showed wrinkled leaves and a flower number reduced by about 50% as compared to the control. *K.pinnata* AAE was a non-transformed wild-type control, *K.pinnata* AAE rol was a rol transformed *K.pinnata* AAE showing dwarfism, wrinkled leaves, delayed flowering and about 50% of the number offlowers a compared to wild-type, having 10 copies of rolC. *K.pinnata* AAE-rol was backcrossed with wild-type AAE resulting in several lines, such as *K.pinnata* Rol-2 Pemba, having intermediate height, but leaves were not wrinkled, and the number of flowers and inflorescences was about the same as of the untransformed *K.pinnata* AAE. The rolC copy number in *K.pinnata* Rol-2 Pemba was determined to be 2. In another experiment, *K.pinnata* AAE was transformed with rol and in the primary transformants, a selection was made on root morphology as described herein, i.e. the root hair length of the selected transformants being at most half of the maximum root hair length observed among the transformants. *K.pinnata* K2 AAE and *K.pinnata* PinS A15 AAE were obtained this way, having a phenotype similar of that of *K.pinnata* Rol-2 Pemba, and having 2 and 3 rolC copies, respectively.

Similar results were obtained for the other plant genera tested, where selection was made also based on root morphology as described above, see table 4.

TABLE 4

Growth habit and their copy number of roIC compared controls

| Sample | FIG. | Growth habit (height) | Average ΔCt | Ratio | Copy number compared to control |
|---|---|---|---|---|---|
| *Solanum tuberosum*[c] | 2a | Normal/control | ND | ND | ND |
| *Solanum tuberosum** rol transformed | 2b | Dwarf | −0.89 | 1.85 | 7 |
| *Solanum tuberosum*** | 2c | Intermediate | 0.22 | 0.6 | 3 |
| *Dipladenia*[c] | 3a | Normal/control | ND | ND | ND |
| *Dipladenia** | 3b | Dwarf | −1.22 | 2.33 | 9 |
| *Dipladenia*** | 3c | Intermediate | −0.25 | 1.18 | 5 |
| *Kalanchoe* int. hyb. 2006-0199[c] | 4a, 5a, 5b | Normal/control | ND | ND | ND |
| *Kalanchoe* int. hyb. 4006-0199K20.1* | 4b, 5b | Dwarf | −1.49 | 2.82 | 11 |
| *Kalanchoe* int. hyb 4006-0199S11** | — | Intermediate height | 1.70 | 0.31 | 1 |
| *Kalanchoe* int. hyb 4006-0199S2** | 4c, 5a | Intermediate height | 2.02 | 0.25 | 1 |
| *Kalanchoe* Ri line 331* | 1d of Christensen 2008, supra | Intermediate | −0.8 | 1.74 | 7 |
| *Kalanchoe pinnata* AAE, wild type[c] | 6 | Normal/control | ND | ND | ND |
| *Kalanchoe pinnata* AAE-rol* | 6 | Dwarf | −1.31 | 2.48 | 10 |
| *Kalanchoe pinnata* rol-2 Pemba*** | 6 | Intermediate height | 1.4 | 0.4 | 2 |
| *Kalanchoe pinnata* Pin5 A15-AAE** | — | Intermediate height | 0.7 | 0.61 | 2 |
| *Kalanchoe pinnata* K2 AAE** | — | Intermediate height | 1.1 | 0.47 | 2 |
| *Rosa hybrida*[c] | 7 | Normal/control | ND | ND | ND |
| *Rosa hybrida** | 7 | Dwarf | −1.68 | 3.20 | 13 |
| *Rosa hybrida*** | 7 | Intermediate | −1.12 | 0.46 | 2 |
| *Aster novi-belgii*[c] | 8 | Normal/control | ND | ND | ND |
| *Aster novi-belgii** | 8 | Dwarf | −1.98 | 3.94 | 16 |
| *Aster novi-belgii*** | 8 | Intermediate | 0.25 | 0.84 | 3 |

[c]control wild type
*rol transformed
**rol transformed and selected for root morphology
***rol transformed and backcrossed with wt Statistical Analysis

*K. pinnata* functioned as a reference of the transformation. Similarly, control explants had five replicates but 5 explants per species/hybrids with a total of 25 per species/hybrids. Since the explants may be taken out of the experiment because of infection, the number of explants changed over time. The total number of explants was therefore monitored to obtain a better ratio between number of explants and formation of roots. The number of roots was monitored as the number increased. The average of surviving explants per petri dish and the average of roots per petri dish were calculated. The two averages were used to calculate a ratio for each petri dish to describe the number of roots per explants.

$V_{max}$ (root development/days) was modeled with a linear regression and using the slope. Standard deviations (SD) and students t-test (t-test) were calculated in Excel for each observation to verify variation within the individual species/hybrids. ANOVA test was performed with R (R is a free software environment for statistical computing).

Results

The experiments involved a natural transformation with *Agrobacterium rhizogenes* to study the transformation efficiency for different species and hybrids and for plain material from in vivo and in vitro. The plants belonging to the species *Strelitzia reginae, Aster novi-belgii, Aster dumosus, Chrysantemum morifolium, Chrysantemum×morifolium* (syn. *C.×grandiflorum* e.g. *Dendranthema* hybrids, or hybrids between *Chrysantemum morifolium* and other *Chrysantemum* species e.g. *Chrysanthemum indicum, Euphorbia pulcherrima, Euphorbia milli, Bouvardia longiflora, Hibiscus rosa-sinensis, Hibiscus schizopetalus, Hibiscus sabdariffa, Hibiscus syriacus, Hibiscus trionum, Hibiscus cannabinus, Mandevilla×amabilis, Mandevilla sanderi, Mandevilla splendens, Nicotiana tabacum, Nicotiana sylvestris, Nicotiana×sanderrae Phalaenopsis amabilis, Phalaenopsis amboinensis, Phalaenopsis aphrodite, Phalaenopsis appendiculata, Vanilla planifolia, Ocimum basilicum, Capsicum annuum, Capsicum baccatum, Capsicum chinense, Capsicum frutescens, Capsicum pubescens, Ipomoea batatas, Solanum lycopersicum, Solanum tuberosum, Solanum nicotiana, Echinacea purpurea, Echinacea angustifolia, Echinacea pallida, Rosa hybrida, Rosa canina, Rosa spinosissima, Rosa damascena "trigintipetala', Rosa centifolia, Schisandra chinensis, Schisandra glabra, Schisandra rubriflora, Rhodiola rosea, Kalanchoe pinnata, Kalanchoe marmorata, Kalanchoe gastonis-bonnieri, Kalanchoe dixoniana, Kalanchoe humilis, Kalanchoe laciniata*, were transformed with the conditions that were found optimal for *K. blossfeldiana* 'Molly' by Christensen et al., (2008, supra) or slightly changed for optimalisation for each of the species. *K. blossfeldiana* 'Molly' was used as a control within the transformants since the cultivar formed background of the transformation system.

Root induction and growth were monitored as a total number of roots per petri dish in each treatment. Since some explants were removed due to infection the total number of explants over time was also monitored. This was done to obtain a more unbiased assessment when calculating the number of roots per explant in each plant line.

Root Development on 0-Media

Root formation was found to take place in the following species; *Strelitzia reginae, Aster novi-belgii, Aster dumosus, Chrysantemum morifolium, Chrysantemum×morifolium* (syn. *C.×grandiflorum* e.g.*Dendranthema* hybrids, or hybrids between *Chrysantemum morifolium* and other *Chrysantemum* species e.g. *Chrysanthemum indicum, Euphorbia pulcherrima, Euphorbia milli, Bouvardia longiflora, Hibiscus rosa-sinensis, Hibiscus schizopetalus, Hibiscus sabdariffa, Hibiscus syriacus, Hibiscus trionum, Hibiscus cannabinus, Mandevilla×amabilis, Mandevilla sanderi, Mandevilla splendens, Nicotiana tabacum, Nicotiana sylvestris, Nicotiana×sanderrae, Phalaenopsis amabilis, Phalaenopsis amboinensis, Phalaenopsis aphrodite, Phalaenopsis appendiculata, Vanilla planifolia, Ocimum basilicum, Capsicum annuum, Capsicum baccatum, Capsicum chinense, Capsicum frutescens, Capsicum pubescens, Ipomoea batatas, Solanum lycopersicum, Solanum tuberosum, Solanum nicotiana, Echinacea purpurea, Echinacea angustifolia, Echinacea pallida, Rosa hybrida, Rosa canina, Rosa spinosissima, Rosa damascena "trigintipetala', Rosa centifolia, Schisandra chinensis, Schisandra glabra, Schisandra rubriflora, Rhodiola rosea, Kalanchoe pinnata, Kalanchoe marmorata, Kalanchoe gastonis-bonnieri, Kalanchoe dixoniana, Kalanchoe humilis, Kalanchoe laciniata*, and was transferred to regeneration medium no later than 100 days After transfer to 0-media. At the time of the first time of transfer to regeneration medium putative transformants from *Strelitzia reginae, Aster novi-belgii, Aster dumosus, Chrysantemum morifolium, Chrysantemum×morifolium* (syn. *C.×grandiflorum* e.g. *Dendranthema* hybrids, or hybrids between *Chrysantemum morifolium* and other *Chrysantemum* species e.g. *Chrysanthemum indicum, Euphorbia pulcherrima, Euphorbia milli, Bouvardia longiflora, Hibiscus rosa-sinensis, Hibiscus schizopetalus, Hibiscus sabdariffa, Hibiscus syriacus, Hibiscus trionum, Hibiscus cannabinus, Mandevilla×amabilis, Mandevilla sanderi, Mandevilla splendens, Nicotiana tabacum, Nicotiana sylvestris, Nicotiana×sanderrae Phalaenopsis amabilis, Phalaenopsis amboinensis, Phalaenopsis aphrodite, Phalaenopsis appendiculata, Vanilla planifolia, Ocimum basilicum, Capsicum annuum, Capsicum baccatum, Capsicum chinense, Capsicum frutescens, Capsicum pubescens, Ipomoea batatas, Solanum lycopersicum, Solanum tuberosum, Solanum nicotiana, Echinacea purpurea, Echinacea angustifolia, Echinacea pallida, Rosa hybrida, Rosa canina, Rosa spinosissima, Rosa damascena "trigintipetala', Rosa centifolia, Schisandra chinensis, Schisandra glabra, Schisandra rubriflora, Rhodiola rosea, Kalanchoe pinnata, Kalanchoe marmorata, Kalanchoe gastonis-bonnieri, Kalanchoe dixoniana, Kalanchoe humilis, Kalanchoe laciniata*, were significantly different from control.

Possible use of Transformed Plants According to the Invention

Kalanchoe

Examples

*Kalanchoe pinnata*

*Kalanchoe marmorata*

*Kalanchoe gastonis*-bonnieri interspefic hybrid 'Tropical Parfait'

*Kalanchoe dixoniana*

*Kalanchoe humilis*

*Kalanchoe laciniata* interspefic hybrid 'Amazing Pink'

Current use primarily as an ornamental plant. A reduced plant height and increased branching was observed as compared to non-transformed plants. Also content of secondary metabolites e.g. bryophillin A, showing strong anti-tumor promoting activity does make this genus/species interesting as a medicinal plant. *Kalanchoe*, in particular *K. pinnata* also contains-coumaric acid, Ferulic acid, Syringic acid, Caffeic acid, citric acid, isocitric acid, malic acid, P-hydroxybenzoic acid, Flavonoids as quercetin, kaempferol, quercetin-3-diarabinoside, kaempferol-3-glucoside, quercetin-3-L-rhamnosido-L-arabino furanoside, η-hentricontane, η-tritriacontane, Sitosterol. Studies showed that several of these compounds exhibited higher concentrations in rol transformed plants.

Any of these compounds can be isolated from *Kalanchoe* and used as or in a human or animal necessity such as a medicament. Plants, transformed with the Ri plasmid of *A. rhizogenes* comprising the rol genes exhibited higher concentrations compared to control.

Rosa

Examples

*Rosa hybrida*
*Rosa canina*
*Rosa spinosissima*
*Rosa damascena* 'Trigintipetala'
*Rosa centifolia*

Current use primarily as an ornamental plant. A reduced plant height and increased branching is observed as compared to non-transformed controls, making it possible to have sufficient branching from fewer cuttings per pot. Rosa is also having significant use in the perfume industry. In Europe, *Rosa damascena* 'Trigintipetala' is particularly used, and *Rosa centifolia* in other parts of the world. The main constituents are the fragrant alcohols geraniol and 1-citronellol and rose camphor. β-Damascenone is also a significant contributor to the scent. Plants, transformed with the Ri plasmid of *A. rhizogenes* comprising the rol genes exhibited higher concentrations compared to control.

Strelitzia

Example

*Strelitzia reginae*

Mainly used as a cut flower because of its size. A significant reduction in plant height and also significantly in production time (time to flowering) is observed in plants, transformed with *Agrobacterium rhizogenes* comprising the Ri plasmid.

Aster

Example

*Aster novi-belgii*
*Aster dumosus*

Mainly used as potted plant and cut flower. A reduced plant height and increased branching is observed as compared to non-transformed controls, making it possible to have sufficient branching from fewer cuttings per pot.

*Chrysantemum*

Examples

*Chrysanthemum morifolium*
*Chrysanthemum indicum*
*Chrysanthemum×morifolium* (*Dendranthema* hybrids)

Mainly used as potted plant and cut flower, but also as ingredient in *Chrysanthemum* tea (*Chrysanthemum indicum*). Reduced plant height and increased branching was observed in transformants making it possible to have sufficient branching from fewer cuttings per pot when using the plants as potted plants. Flavor of tea extracts made from Ri-transformed *Chrysanthemum indicum* and *Chrysanthemum morifolium* appeared to be more intense than that of not transformed counterparts.

Euphorbia

Example

*Euphorbia milli*
*Euphorbia pulcherrima* (Poinsettia)

Mainly used as an ornamental plant. A reduced plant height and increased branching was observed as compared to non-transformed plants, making it possible to have sufficient branching without pinching and from fewer cuttings per pot.

Hibiscus

Examles

*Hibiscus rosa-sinensis*
*Hibiscus schizopetalus*
*Hibiscus sabdariffa*
*Hibiscus syriacus*
*Hibiscus trionum*
*Hibiscus cannabinus*

Mainly used as potted plant or ornamental garden plants in temperate areas (*Hibiscus syriacus*) and in the tropics/subtropics (all species). Reduced plant height and increased branching is observed in transformants making it possible to have sufficient branching without pinching and from fewer cuttings per pot. Hibiscus flowers contain anthocyanins, and plants transformed with the Ri plasmid of *A. rhizogenes* comprising the rol genes exhibited higher concentrations as compared to control.

Dipladenia/Mandevilla

Examples

*Mandevilla×amabilis*
*Mandevilla sanderi*
*Mandevilla splendens*

Mainly used as potted plant or ornamental garden plants in tropics/subtropics. In transformants, reduced plant height and increased branching was observed making it possible to have sufficient branching without pinching and from fewer cuttings per pot. Costly work attaching the plants to a physical fixture will not be needed in rol transformants.

Nicotiana

Examples

*Nicotiana tabacum*

Mainly used as crop plants for the production of tabacco. Tobacco leaves normally contain 2 to 8% nicotine and plants, transformed with the Ri plasmid of *A. rhizogenes* comprising the rol genes exhibited higher concentrations compared to control.

*Nicotiana sylvestris*
*Nicotiana×sanderrae,*

Mainly used as ornamental/bedding plants. A reduced plant height and increased branching was observed making it possible to have sufficient branching without pinching and from fewer cuttings per pot.

Bouvardia

Example

*Bouvardia longiflora*

Mainly used as potted plant and cut flower. In trasformed plants, a reduced plant height and increased branching is observed making it possible to have sufficient branching from fewer cuttings per pot with less chemical growth regulation needed.

Phaelanopsis

Example

*Phalaenopsis amabilis*
*Phalaenopsis amboinensis*
*Phalaenopsis Aphrodite*
*Phalaenopsis appendiculata*

Used as potted plant and cut flower, the largest potted plant product (produced numbers and turnover) in Europe. A reduced plant height and increased branching was observed in transformed plants, making it possible to have more spikes per plant using less chemical growth regulation with expected higher prices on the market.

*Vanilla planifolia*

Vanilla is one of the primary sources for vanilla flavouring, due to its high vanillin content (4-hydroxy-3-methoxybenzaldehyde) and plants, transformed with the Ri plasmid of *A. rhizogenes* comprising the rol genes exhibited higher concentrations compared to control.

Basil

Example

*Ocimum basilicum*

Mainly used as an edible plant. The leaves may taste somewhat like anise, with a strong, pungent, often sweet smell, due to its content of metylchavicol, kineol and linalool. Plants, transformed with the Ri plasmid of *A. rhizogenes* comprising the rol genes exhibited higher concentrations compared to control.

Capsicum

Examples

*Capsicum annuum,*
*Capsicum baccatum,*
*Capsicum chinense,*
*Capsicum frutescens,*
*Capsicum pubescens.*

Mainly used as spices and food vegetables, but Capsicum containing capsaicin (methyl vanillyl nonenamide), has also found use in medicines to stimulate blood circulation or to relieve pain. Plants, transformed with the Ri plasmid of *A. rhizogenes* comprising the rol genes exhibited higher concentrations compared to control.

Ipomoea

Example

*Ipomoea batatas*

Known as sweet potato. Its large, starchy, sweet-tasting, tuberous roots are a root vegetable. Besides starches, sweet potatoes are rich in complex carbohydrates, dietary fiber and in beta-carotene (a provitamin A carotenoid), while having moderate contents of other micronutrients, including vitamin B5, vitamin B6, manganese and potassium. Plants, transformed with the Ri plasmid of *A. rhizogenes* comprising the rol genes exhibited higher concentrations compared to control.

Tomato

Example

*Solanum lycopersicum*

The tomato is the edible, often red/orange/yellow/greenish fruit/berry. The fruit contains lycopene, a powerful antioxidant, has been linked with reduced risks of colorectal, gastric, lung, prostate, and pancreas cancer. We observe reduced plant height and increased branching making it possible to use the plant also as a houseplant with edible fruits or in gardens with limited space available. Furthermore we noticed that content of lycopene increased in fruits of plants, transformed with the Ri plasmid of *A. rhizogenes* comprising the rol genes.

Potato

Example

*Solanum tuberosum*

The potato is and edible plant, containing vitamins and minerals, as well as an assortment of phytochemicals, such as carotenoids and natural phenols. Reduced plant height and increased branching was observed making it possible to use the plant also as a garden plant with edible tubers in gardens with limited space available Furthermore it was noticed that content of vitamin and mineral content increased in tuber of rol transformed potato plants. Also, a more intense taste was observed.

*Solanum nicotianum*

*Solanum nicotianum* is an intergeneric graft chimera of *Nicotiana tabacum* L. and *Solanum laciniatum* (Kaddoura, R. L. and Mantell, S. H., (1991) Ann Bot 68 (6): 547-556, and used as an ornamental plant. A reduced plant height and increased branching is observed as compared to non-transformed controls, making it possible to have sufficient branching from fewer cuttings per pot.

Echinacea

Examples

*Echinacea purpurea*
*Echinacea angustifolia,*
*Echinacea pallida*

Echinacea is mainly used for herbal medicines—containing phenyl propanoid, echinacoside. The constituent base for Echinacea is complex, consisting of a wide variety of chemicals of variable effect and potency. The range of active substances have antimicrobial, stimulating or modulating effects on different parts of the immune system. All species contain phenols, phenyl propanoid constituents such as cichoric acid and caftaric acid are present in *E. purpurea*, other phenols include echinacoside. Other chemical constituents that may be important in echinacea health effects include alkylamides and polysaccharides. The immunomodulatory effects of echinacea preparations are likely caused by fat-soluble alkylamides (alkamides), Alkylamides have similar potency to that of THC at the CB2 receptor, with THC being around 1.5 times stronger (~40 nm vs ~60 nm affinities). However, potency is dramatically less than that of THC at the psychoactive CB1 receptor (~40 nm vs ~>1500 nm affinities). It was now observed that concentration of a range of chemical content increased in parts of plants, transformed with the Ri plasmid of *A. rhizogenes* comprising the rol genes. Furthermore plant height and increased branching was observed making it possible to use the plant also as a house/garden plant with ornamental value.

*Schisandra*

Examples

*Schisandra chinensis*
*Schisandra glabra*
*Schisandra rubriflora* (ornamental use)

The berries of Schisandra are used in traditional Chinese medicine. Chemical constituents include the lignans schisandrin, deoxyschisandrin, gomisins, and pregomisin, which are found in the seeds of the fruit. It was observed that concentration of a range of chemical content increased plant parts of plants, transformed with the Ri plasmid of *A. rhizogenes* comprising the rol genes. Furthermore plant height and increased branching was observed, making it possible to use the plant also as a house/garden plant with ornamental value.

*Rhodiola*

Example

*Rhodiola rosea*

Rhodiola has been used in herbal medicine in China, Russia and Scandinavia to better cope with the cold Siberian weather. The aerial portion is consumed as food in some parts of the world, sometimes added to salads. The root and other plant parts contain rosavin, rosarin, rosin and salidroside (and sometimes p-tyrosol, rhodioniside, rhodiolin and rosiridin. It was observed that the concentration of a range of chemical contents increased in plant parts of rol transformed plants. The plant is quite slow growing and the ornamental value of the plant is limited.

Elevated Flavonoid Levels in *Kalanchoe*

Wild type *Kalanchoe* pinnate and the transformed counterpart having 5 Ri gene copies as described in table 4 (i.e. obtained by backcrossing a primary Ri transformed *K.pinnata* with wild type untransformed *K.pinnata*) were taken and extracts were prepared by freeze drying 50 g leaves until the water loss was 85 w/w %, followed by incubation in methanol (5 weight parts methanol perweight part dried leaves) overnight in the dark at 5° C. The supernatant was collected and evaporated under pressure to complete dryness. Extract samples were prepared with a concentration of 100 mg/ml methanol and filtered (Sartorius, 0.20 μm). HPLC-MS/MS analysis (a combination of of high-performance liquid chromatography (HPLC) with mass spectrometry (MS), MS/MS being the combination of two mass analyzers in one mass spec instrument) was used to identify the different derivatives of the flavonoids according to their characteristic masses of the deprotonated molecular ions. [M-HT were used for identification, based on mass-to charge ratio (m/z; Quercetin=301; Isorhamnetin=315; Kaempferol=285). HPLC-MS/MS was performed in accordance with Tsimogiannis et al. (Molecules (2007) 12, 593-606.

It was found that in wild type *K. pinnata*, the levels of kaempferol and isohamnetin were 2,12 and 4,74 μg per g plant material, respectively, whereas in the *K.pinnata* determined to have 5 copies of Ri genes, the said level were 2,41 and 6,03 μg per g plant material, respectively.

The invention claimed is:

1. A method for the preparation of a plant comprising, in the genome thereof, at least 1 but no more than 5 copies of all the genes present on the Ri plasmid, comprising the steps of:
(a) transforming tissue of the wild type plant with the Ri plasmid of *Agrobacterium rhizogenes*,
(b) allowing the transformed tissue to develop roots having a hairy phenotype,
(c) selecting, among the roots with hairy phenotype of step (b), a root where the hairy phenotype shows a maximum root hair length of at most half of the maximum root hair length observed in the roots obtained in step (b);
(d) growing the selected root on a regeneration medium and allowing a transformed rooted plantlet to generate from the said selected root;
(e) growing said transformed rooted plantlet into a mature transformed mother plant having a height of 25-75% of that of the corresponding wild type plant of step (a) and having not less than 80% of the number of flowers of the corresponding wild type plant of step (a); and
(f) optionally, generating progeny of said plant of (e).

2. The method of claim 1, wherein step (c) further comprises selecting, among the roots with hairy phenotype of step (b), a root where the hairy phenotype shows a number of branches per length that is at most half of the maximum number of branches per such length observed in the roots obtained in step (b).

3. The method of claim 1, wherein step (e) further comprises selecting for plants or progeny not having a delayed flowering time by more than 4 days as compared to the corresponding wild type plant of step (a).

4. The method of any of claim 1, the selection further comprising assaying the number of copies of the genes originating from the Ri plasmid of *Agrobacterium rhizogenes*.

5. A method for the preparation of a plant comprising, in the genome thereof, at least 1 but no more than 5 copies of all the genes present on the Ri plasmid, comprising the steps of:
(a) transforming tissue of the wild type plant with the Ri plasmid of *Agrobacterium rhizogenes*,
(b) allowing the transformed tissue to develop roots having a hairy phenotype,
(c) selecting a putatively transformed root having a hairy root phenotype;
(d) growing the selected root on a regeneration medium and allowing transformed rooted plantlet to generate from the said selected root;
(e) growing said transformed rooted plantlet into a mature transformed mother plant;
(f) generating progeny of the mature transformed mother plant of step (e) by crossing, backcrossing and selfing, while selecting for progeny having an increased height as compared to the mature transformed mother plant of step (e) and a reduced height as compared to that of the corresponding wild type plant of step (a), and (g) repeating step (f) until the progeny results in mature plants having a height of 25-75% of that of the corresponding wild type plant of step (a) and having not less than 80% of the number of flowers of the corresponding wild type plant of step (a), and having in the genome thereof, at least 1 but no more than 5 copies of the Ri plasmid.

6. The method of claim 5, wherein step (f) and/or (g) further comprises selecting for plants or progeny not having a delayed flowering time by more than 4 days as compared to the corresponding wild type plant of step (a).

7. The method of claim 5, the selection further comprising assaying the number of copies of the genes originating from the Ri plasmid of *Agrobacterium rhizogenes*.

8. The method according to claim 1, wherein said plant comprises, in the genome thereof, at least 1 but no more than 3 copies of the Psi plasmid.

9. The method according to claim 5, wherein said plant comprises, in the genome thereof, at least 1 but no more than 3 copies of the Ri plasmid.

\* \* \* \* \*